United States Patent [19]
Evanson et al.

[11] Patent Number: 5,331,278
[45] Date of Patent: Jul. 19, 1994

[54] APPARATUS FOR INSPECTING DEGRADATION/DAMAGE OF A MATERIAL USING AN AC MAGNET, A SUPERCONDUCTING DC MAGNET AND A SQUID SENSOR

[75] Inventors: Stephen Evanson, Garden Suburbs Oldham, England; Satoshi Kanno; Masahiro Otaka, both of Hitachi, Japan; Toshihiko Yoshimura, Tsuchiura, Japan; Kunio Hasegawa, Katsuta, Japan; Kazuo Takaku, Hitachi, Japan

[73] Assignee: Hitachi, Ltd., Tokyo, Japan

[21] Appl. No.: 757,585

[22] Filed: Sep. 11, 1991

[30] Foreign Application Priority Data

Sep. 11, 1990 [JP] Japan .................................. 2-239061
Sep. 11, 1990 [JP] Japan .................................. 2-240290

[51] Int. Cl.⁵ ...................... G01N 27/72; G01R 33/12; G01R 33/035; G21C 17/003
[52] U.S. Cl. ........................ 324/232; 324/248; 324/240
[58] Field of Search ................. 324/248, 232, 239–243

[56] References Cited

U.S. PATENT DOCUMENTS

| | | | |
|---|---|---|---|
| 2,346,830 | 4/1944 | DeLanty | 324/232 |
| 3,281,666 | 10/1966 | Mahino | 324/232 |
| 3,588,683 | 6/1971 | Lloyd | 324/232 |

FOREIGN PATENT DOCUMENTS 2-78983  3/1990  Japan .................................. 324/248

*Primary Examiner*—Walter E. Snow
*Attorney, Agent, or Firm*—Antonelli, Terry, Stout & Kraus

[57] ABSTRACT

A non-destructive inspection apparatus includes a magnetic field applying device and a magnetic sensor. The magnetic field applying device is adapted to apply DC and AC magnetic fields to an object to be inspected. Degradation/damage of the object is detected by measuring a magnetic characteristic of the object in a state in which the DC and AC magnetic fields are applied. Also, a non-destructive inspection apparatus includes as a magnetic sensor a plurality of pickup coils and a SQUID(s) connected to the pickup coils and decides the form of a defect of an object to be inspected by producing a difference between outputs of the pickup coils or SQUIDs.

17 Claims, 22 Drawing Sheets

OUTPUT WAVEFORM
OF DC POWER
SOURCE

OUTPUT WAVEFORM
OF AC POWER
SOURCE

OUTPUT WAVEFORM
OF DC POWER
SOURCE

OUTPUT WAVEFORM
OF AC POWER
SOURCE $H_1 < H_2 < H_3$

APPARATUS FOR INSPECTING DEGRADATION/DAMAGE OF A MATERIAL USING AN AC MAGNET, A SUPERCONDUCTING DC MAGNET AND A SQUID SENSOR

BACKGROUND OF THE INVENTION

The present invention relates to an inspection apparatus which non-destructively inspects degradation (artificial aging embrittlement) and/or strain damages, or defects in a structure or a practical equipment member by use of a SQUID (superconducting quantum interference device).

One example of the conventional method for detection of the embrittlement (or degradation) of a metal material is disclosed by JP-A-54-61981. In the disclosed method, the presence/absence of the embrittlement of a weld metal of austenitic stainless steel is decided in accordance with whether or not the quantity of δ ferrite has been reduced from its initial value by at least 5%.

Non-destructive inspection of defects using SQUID's is discussed by Weinstock et al. in SQUID'85-Superconducting Quantum Interference Devices and their Applications, 853-856, 1985 Walter de Gruyter & Co., Berlin-New York printed in Germany. The other prior art references relevant to non-destructive inspection of defects using SQUID's include JP-A-63-235876 JP-A-63-32384, JP-A-60-147646 and JP-A-60-58565. These references disclose the use of pickup coils having a higher-order differential coil structure.

SUMMARY OF THE INVENTION

An object of the present invention is to provide an inspection apparatus which non-destructively inspects degradation (artificial aging embrittlement) and/or strain damages, or defects in a structure or a practical equipment member by use of a SQUID.

Another object of the present invention is to provide an inspection apparatus which enables non-destructive and highly-precise detection of the degree of embrittlement (degradation) and/or the degree of strain damage of a structure or a practical equipment member which is used under high-temperature environments and is made of a metal material such as strainless steel with ferrite phase or duplex strainless steel or low alloy steel.

A further object of the present invention is to provide a non-destructive inspection apparatus which can detect defects while reducing background noises.

A still further object of the present invention is to provide a non-destructive inspection apparatus which can decide the form or the kind of a defect (and the surface area of the defect) with a high precision and by a single scan.

Taking as an example a stainless steel with ferrite phase among metal materials which are handled by the JP-A-54-61981 and are used at high temperatures, it is known that the stainless steel with ferrite phase encounters aging embrittlement when it is used for a long time at high temperatures. This aging embrittlement is due to the generation of σ embrittlement at relatively high temperatures beyond 600° C. caused by the precipitation of σ phase and the generation of so-called 475° C. brittleness in a range of 400° C. to 500° C. There is a possibility that the 475° C. brittleness may be generated even in a range of temperatures lower than 400° C. if the stainless steel with ferrite is used for a long time. Therefore, sufficient consideration is required in using a practical equipment member made of stainless steel with ferrite at high temperatures. However, in the prior art, no consideration is paid to embrittlement at temperatures lower than 500° C. and strain aging in the case where there is a strain. Therefore, there is a problem that it is not possible to detect the degree of 475° C. brittleness.

Also, in the prior art, the initial quantity of ferrite in a weld zone of the practical equipment is different depending on a welding position and the variation in quantity is large. Further, the practical equipment includes a great number of welded locations or weld zones. Therefore, it is difficult to entirely monitor the initial quantities of ferrite in all the weld zones and the equipment materials. Accordingly, there is a problem that the prior art is not applicable to a location where the initial quantity of ferrite is not known and hence it cannot be put to practical use in the practical equipment.

Therefore, the present invention aims at the provision of a metal material degradation/damage inspection apparatus which enables non-destructive and highly-precise detection of the degree of embrittlement and/or the degree of strain damage of a practical equipment member which is used under high-temperature environments and is made of a metal material such as stainless steel with ferrite or low alloy steel.

To attain this object, in a metal material degradation/damage inspection apparatus according to the present invention, a change (ΔB-ΔH curve) of a magnetic hysteresis loop (B-H curve) in a small region thereof (or a so-called minor hysteresis loop) exhibiting a magnetic characteristic of a material to be inspected is measured to detect the thermal age degradation and/or strain damage of the material from the value of ΔB/≢H and the degree of degradation and/or the degree of damage of the material are decided on the basis of the measured magnetic characteristic of the material. In order to measure ΔB/ΔH of the magnetic hysteresis loop exhibiting the magnetic characteristic of the material to be inspected, the apparatus comprises a sensor section including in combination a DC magnet for applying a DC magnetic field to the material to be inspected, a small-sized AC magnet for applying a small AC magnetic field and a magnetic sensor of differential type or the like for measuring the magnetism. The apparatus further comprises a processing unit for deciding the degree of degradation and/or the degree of damage of the material on the basis of measurement data obtained by the sensor section.

For inspection of the material of an equipment in a practical plant, the apparatus may further comprise a scanner for scanning the sensor section on the equipment.

The sensor section may include the small-sized AC magnet, the magnetic sensor and the DC magnet arranged in the mentioned order from the material or object side in order to apply the DC magnetic field to the material or object uniformly over a wide range and to apply the weak AC magnetic field locally.

The sensor may use a horseshoe-shaped yoke in order to magnetize the object with a high efficiency and to effect transverse magnetization.

For simplification of the sensor structure, a magnetizing current including a DC component added with a small AC component may be used as a magnetizing current of the DC magnet, thereby removing the small-sized Ac magnet.

The magnetic sensor may be of a differential type in order to detect only the weak AC magnetic field with a high sensitivity.

For non-contact and high-sensitivity measurement, a SQUID (superconducting quantum interference device) sensor and a superconducting magnet may be used for the magnetic sensor and the DC magnet, respectively.

The processing unit may statistically process $\Delta B/\Delta H$ of the magnetic hysteresis loop and parameters of $\Delta B/\Delta H$ curves in order to estimate the degree of degradation and/or the degree of damage of the object to be inspected.

The principle of the operation and the functions of the metal material degradation/damage inspection apparatus according to the present invention will be explained by virtue of the B-H curve of a metal material shown in FIG. 13. When a metal material is used for a long time under high-temperature environments, a change of the internal structure is generated with a decrease of the strength. It is known that the change in internal structure is attended with a change in electromagnetic characteristics including the electric resistivity $\rho$ and the magnetic permeability $\mu$.

However, in a practical plant operated at relatively low temperatures, the degree of embrittlement caused by thermal aging is small and a change in electromagnetic characteristic is also small. Therefore, the present inventors have measured the $\Delta B_i$-$\Delta H_i$ characteristic as a small magnetic hysteresis quantity as shown in FIG. 13. As a result, it has been found out that a good correspondence exists between the age embrittlement of the material and the $\Delta B_i$-$\Delta H_i$ characteristic thereof when a DC magnetic field is $H_i$.

Also, when plastic strain by processing is applied to a metal material such as stainless steel with ferrite phase or low alloy steel, the magnetic characteristic $\Delta B$-$\Delta H$ of the material changes depending on the quantity of plastic strain. Further, in the case where a material beforehand applied with a strain is aged, a change in magnetic characteristic $\Delta B$-$\Delta H$ corresponding to the degree of strain aging is exhibited.

In other words, if the above phenomena are utilized, it is possible to detect the degrees of progression of aging embrittlement and/or processing strain of a metal material such as stainless steel with ferrite phase or low alloy steel with a high precision.

In the apparatus according to the present invention, the DC magnet applies a base magnetic field $H_i$ to the object to be inspected, as shown in FIG. 13. On the other hand, the small-sized AC magnet applies a weak AC magnetic field $\Delta H_i$ to the object. A change $\Delta B_i$ of the magnetic flux density of the object at this time due to the weak AC magnetic field $\Delta H_i$ is detected by the magnetic sensor. Thereby, it is possible to measure the small magnetic hysteresis characteristics $\Delta B$-$\Delta H$ of degraded/damaged materials (or objects). The processing unit can estimate the degree of degradation/damage of the object by comparing data of the measured magnetic characteristic with a data base beforehand prepared. As a result, the detection of the degree of degradation and/or the degree of damage of the object becomes possible.

The scanner scans the sensor section on the object or equipment to be inspected, thereby making measurement and inspection in a practical plant possible.

The use of the horseshoe-shaped yoke in the sensor section makes transverse magnetization and highly-efficient magnetization. The similar effect can be obtained by using the superposition of a DC component and a small AC component as a magnetizing current to be applied to the DC magnet.

The similar effect can be obtained in a remote measurement by using the combination of a SQUID (superconducting quantum interference device) sensor, a DC superconducting magnet and a small-sized AC normal-conducting magnet in the sensor section. Also, the use of a differential type magnetic sensor cancels the DC component, thereby making it possible to detect only the small AC component with a high sensitivity.

According to the present invention, the degree of embrittlement and/or the quantity of stain of a metal material used at high temperatures can be detected non-destructively and rapidly. Therefore, it is possible to prevent the damage of a practical equipment from occurring, thereby improving the safety of the equipment.

The prior art relevant to non-destructive inspection of defects involves a problem that a signal originating from the defect (or a defect signal) superposes on a background signal induced by the surface geometry (or general surface unevenness) of a steel plate or specimen. The background signal is very large whereas the defect signal is relatively small. Accordingly, in order to detect the defect signal by use of a SQUID having a very high sensitivity, the measuring range must be reset many times. The resetting brings with it a detection error of a certain degree. Also, in the case where the defect signal is considerably small, there is a problem that the defect signal may be buried in the background signal.

Further, in the conventional apparatus, it is difficult to determine the surface area of a defect by a single scan. A plurality of scans are conducted and the results of the scans are combined or synthesized to determine the surface area of the defect.

Therefore, the present invention aims at the provision of a non-destructive inspection apparatus with SQUID which can reduce background noises and aims at the provision of such an apparatus which can decide the form or the kind of a defect (and the surface area of the defect) by a single scan.

To attain this object, in a non-destructive inspection apparatus with SQUID according to the present invention, a plurality of pickup coils provided at different distances from an object to be inspected are used as a gradiometer in order to minimize the background signal. A scheme of measuring a difference between signals include a method in which SQUID's are respectively provided for the pickup coils and a difference between outputs of the SQUID's is produced and a method in which the pickup coils are connected to provide a difference between the coil outputs as a sensor output and the sensor output is amplified by a SQUID.

According to one aspect of the present invention, a non-destructive inspection apparatus with SQUID comprising a pickup coil for detecting a magnetic flux signal from an object to be inspected, a SQUID for receiving a signal from the pickup coil and a processing unit for receiving and processing an output signal from the SQUID is characterized in that a plurality of pickup coils are provided at different distances from the object SQUID's are respectively provided for the plural pickup coils, and the processing unit performs an operation to minimize a background signal caused by the surface geometry of the object by producing a difference between outputs of the SQUID's.

According to another aspect of the present invention, a non-destructive inspection apparatus with SQUID comprising a pickup coil for detecting a magnetic flux signal from an object to be inspected, a SQUID for receiving a signal from the pickup coil and a processing unit for receiving and processing an output signal from the SQUID is characterized in that a plurality of pickup coils are provided at different distances from the object, SQUID's are respectively provided for the plural pickup coils, and the processing unit decides the form of a defect of the object from a measured output value of each SQUID on the basis of a predetermined relationship between SQUID output value, distance from object and configuration of defect of object.

According to a further aspect of the present invention, a non-destructive inspection apparatus with SQUID comprising a pickup coil for detecting a magnetic flux signal from an object to be inspected, a SQUID for receiving a signal from the pickup coil and a processing unit for receiving and processing an output signal from the SQUID is characterized in that at least one pair of pickup coils are provided at different distances from the object and with different directions of winding, a SQUID is provided for the coil pair having different directions of winding, and the processing unit decides the form of a defect of the object from a measured output value of the SQUID on the basis of a predetermined relationship between SQUID output value, distance from object and configuration of defect of object.

In the above non-destructive inspection apparatus, the processing unit can determine the surface area of the defect from the decided configuration of the defect on the basis of a predetermined relationship between area of defect and SQUID output. It is preferable that a distance (h) between the object and the pickup coil is between 20 to 100 mm and an interval ($\Delta$) between the pickup coils is between 2 to 10 mm. Also, it is preferable that the distance (h) between the object and the pickup coil and the interval ($\Delta$) between the pickup coils satisfy the condition of $10 \leq h/\Delta \leq 20$.

Provided that the distance between an object and a pickup coil is h, a relationship between SQUID output V and h in the case of the absence of a defect is represented by equation (1):

$$V_N = ah^{-1} \tag{1}$$

where $\alpha$ is a constant.

On the other hand, a relationship between V and h in the case of the presence of a defect is represented by equation (2) in the case of a rectangular defect or equation (3) in the case of a circular defect:

$$V_S = \beta h^{-3.5} \tag{2}$$

or $$V_H = \gamma h^{-5} \tag{3}$$

where $\beta$ and $\gamma$ are constants. Grounds for equations (1) to (3) will now be shown.

The present inventors have studied the properties of various defect signals. As shown in FIGS. 29 to 31, plates having background noises or no defect (FIG. 29), a slit (FIG. 30) and a hole (FIG. 31) were respectively disposed below SQUID sensors and an output of the SQUID was measured while making movement in a direction of h. The results of measurement is shown in FIG. 32.

When a relationship between the SQUID output V and the position h is represented by $$V = ah^x \tag{A}$$

or $$\log V = \log a + x \log h, \tag{B}$$

$x = -1$, $x = -3.5$ and $x = -5$ and determined for the background noises, slit and hole, respectively, from the gradients of lines shown in FIG. 32. Thus, it has been found out experimentally that the SQUID output changes depending on the form or the kind of a defect.

In a non-destructive inspection SQUID magnetometry, there is measured a SQUID output when a sensor including a pickup coil is horizontally scanned. The surface of an object to be inspected is not always flat. Accordingly, when the sensor is scanned, a distance h between the sensor and the object changes depending on the unevenness of the surface of the object and the SQUID output changes as represented by equation (1) even in the case where any defect is not present. This is a background signal. In order to minimize the background signal, a sensor is provided with a plurality of pickup coils at different distances from the object to be inspected. For example, in the case where two pickup coils are used and SQUID's are respectively provided for the two pickup coils, the outputs of individual SQUID's are derived from equation (1) as follows:

$$V_{N1} = ah^{-1} \tag{4}$$

and $$V_{N2} = a(h+\Delta)^{-1} \tag{5}$$

where $\Delta$ is an interval between the two pickup coils. Taking a difference between both the SQUID outputs, we obtain $$V_{N1} - V_{N2} = a \frac{\Delta}{h(h+\Delta)}. \tag{6}$$

Now, set $\Delta/h_0$ to 1/10 as an example where $h_0$ is an initial setting distance between the pickup coil and the object. Then, $\Delta/h$ is about 1/10 since $h \approx h_0$. Accordingly, equation (6) can be rewritten by $$V_{N1} - V_{N2} \approx 0.091 ah^{-1}. \tag{7}$$

The value of equation (7) is about 1/10 of that of equation (1). Namely, it is possible to make the background signal small. If $\Delta/h_0$ is set to 1/20, the background signal can be reduced to about 1/20. In other words, the measurement of a difference between SQUID outputs results in the reduction of a background signal substantially conformable to the value of $\Delta/h_0$.

In the case where there is a defect, or more especially, a rectangular defect, the outputs of individual SQUID's at a location where the defect exists are derived from equation (2) as follows:

$$V_{S1} = \beta h^{-3.5} \tag{8}$$

and $$V_{SA2} = \beta(h+\Delta)^{-3.5}. \tag{9}$$

Provided that $\Delta/h \% 1/10$, like in the above, a difference between both the SQUID outputs is as follows:

$$V_{S1} - V_{S2} \approx 0.283\beta h^{-3.5}. \quad (10)$$

In the case of a circular defect, the outputs of individual SQUID's are derived from equation (3) as follows:

$$V_{H1} = \gamma h^{-5} \quad (11)$$

and $$V_{H2} = \alpha(h+\Delta)^{-5}. \quad (12)$$

Provided that $\Delta/h \% 1/10$, like in the above, a difference between both the SQUID outputs is as follows:

$$V_{H1} - V_{H2} \approx 0.379\gamma h^{-5}. \quad (13)$$

The value of equation (10) is about ¼ of that of equation (2), and the value of equation (13) is about ⅜ of that of equation (3). Accordingly, the use of a difference between SQUID's outputs makes a defect signal (or a signal originating from a defect) small but the reduction of the defect signal is smaller than the above-mentioned reduction (about 1/10) of the background signal induced by the surface geometry (or unevenness) of the object to be inspected. From the foregoing, it can be understood that the measurement of a difference between SQUID outputs has an effect of enhancing the defect signal.

The above effect similarly holds for the case where a plurality of connected pickup coils are provided. When a sensor is constructed by two pickup coils, the directions of winding of the coils are made reverse to each other. Accordingly, a magnetic field generates currents of reverse directions in the pickup coils and a difference between outputs of the pickup coils becomes an output of the sensor body. This sensor output is amplified by a SQUID. In this case, the number of times of change-over (or resetting) of the measuring range of the SQUID can be reduced greatly. Accordingly, there is provided an effect that it is possible to reduce a measurement error which may attend on the resetting.

Further, since a SQUID output signal depending on a measuring position is different in accordance with the background and the form or the kind of a defect, as shown by equations (1) to (13), it is possible to identify the signal or to decide the kind or type of the signal. Namely, the detection of the form of a defect and the measurement of the surface area of the defect by a single scan become possible by using an experimentally revealed property that a relationship between a distance from an object to be inspected and a SQUID output depends on the form of the defect.

According to the present invention, there is an effect that a background signal depending on the surface geometry of an object to be inspected can be reduced greatly. Further, since a SQUID is connected for each pickup coil or each pickup coil pair, it is possible to determine the form and the area of a defect by a single scan. Further, in the case where a SQUID is connected to at least one pair of two connected pickup coils having different directions of winding, there is an effect that the number of times of change-over of the measuring range is greatly reduced, thereby improving the precision of measurement.

DESCRIPTION OF THE PREFERRED EMBODIMENTS

Embodiments of the present invention will now be explained in reference to the accompanying drawings.

Figure 1:
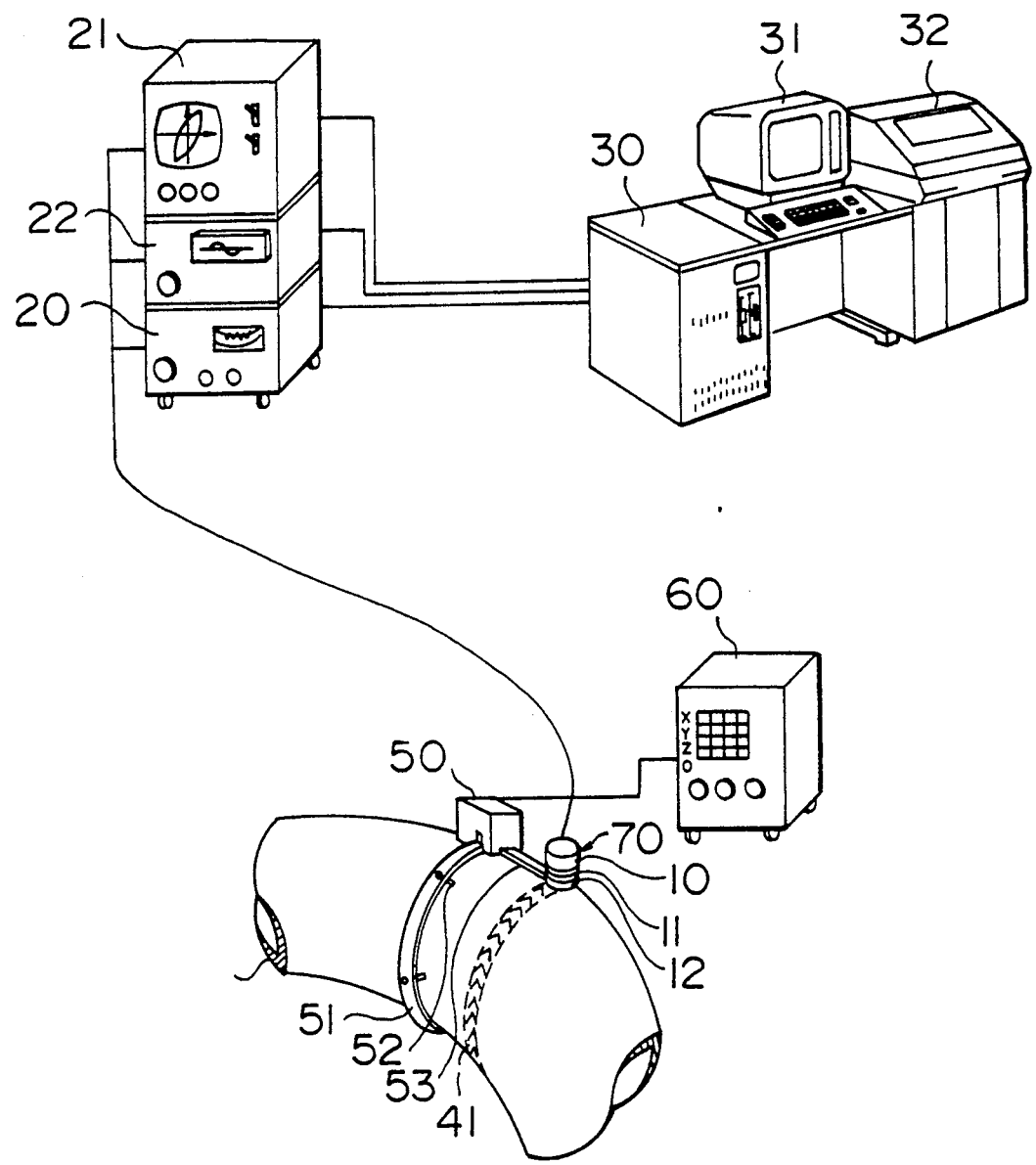
FIG. 1 is a perspective view systematically showing the overall construction of an embodiment of a metal material degradation/damage inspection apparatus according to the present invention.

FIG. 1 is a perspective view systematically showing the overall construction of an embodiment of a metal material degradation/damage inspection apparatus according to the present invention. In FIG. 1, the apparatus detects the condition of degradation/damage of a weld zone 41 of an object 40 to be inspected which may be a pipe or the like used in a nuclear power plant. For this purpose, a sensor section 70 including a DC magnet 10, a magnetic sensor 11 and a small-sized AC magnet 12 is arranged on/above the weld zone 41. The sensor section 70 is attached to a scanner 50 through a sensor bar 53 so that the sensor section 70 can be scanned in an axial direction of the object or pipe 40 by virtue of a telescopic motion of the sensor bar 53. A rail 51 is fixed on the pipe 40 by means of stands 52 so the scanner 50 can move on the rail 51. Namely, the sensor 70 can be scanned in axial and circumferential directions of the pipe 40 by the scanner 50. The scanner 50 is position-controlled by a scan controller 60. The DC magnet 10, the magnetic sensor 11 and the small-sized AC magnet 12 of the sensor section 70 are connected to a DC power source 20, a sensor controller 21 and an AC power source 22, respectively. The DC power source 20, the sensor controller 21 and the AC power source 22 are connected to a computer 30 and the result of measurement is displayed on a display 31 of the computer 30 and/or outputted by an output device 32 of the computer 30.

Next, the details of embodiments of the sensor section 70 shown in FIG. 1 will be explained by use of FIGS. 2 to 10.

Figure 2:
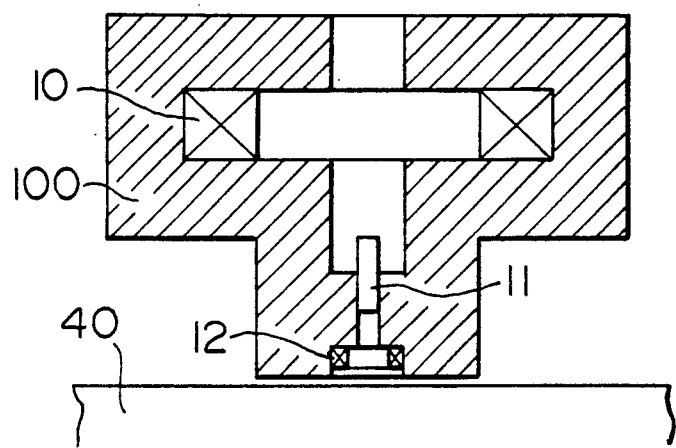
FIG. 2 is a detailed cross section showing a first embodiment of a sensor section shown in FIG. 1.

FIG. 2 is a detailed cross section of a first embodiment of the sensor section 70 shown in FIG. 1. More especially, FIG. 2 shows an embodiment of a coaxial type sensor section. A small-sized AC magnet 12 is arranged in the vicinity of the surface of an object (or pipe) 40 to be inspected to magnetize the object 40. The small-sized AC magnet 12 is driven at a low frequency lower than several Hz's in order that an eddy current is not generated in the object 40. A small change of the magnetic characteristic (or magnetism) of the object (or pipe) 40 attendant upon the degradation/damage thereof is detected by a magnetic sensor 11 positioned above the small-sized AC magnet 12. A DC magnet 10 to apply a base magnetic field to the object 40 is arranged above the magnetic sensor 11. The DC magnet 10, the magnetic sensor 11 and the small-sized AC magnet 12 are integrated by a sensor holder 100 made of a non-magnetic insulating material.

Figure 3:
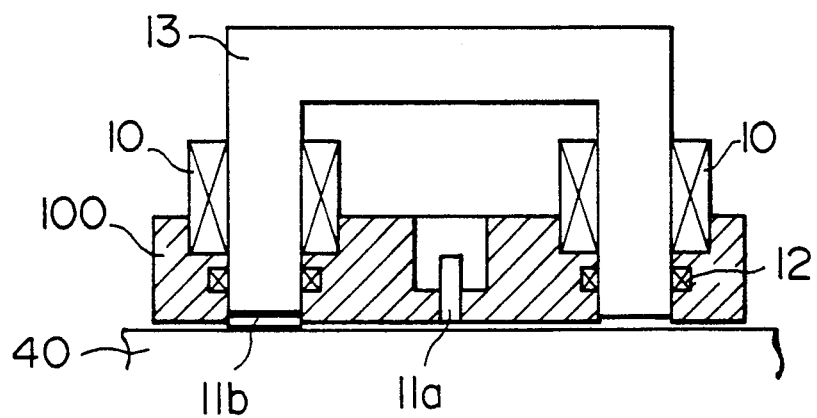
FIG. 3 is a detailed cross section showing a second embodiment of the sensor section shown in FIG. 1.

FIG. 3 is a detailed cross section of a second embodiment of the sensor section 70 shown in FIG. 1. More especially, FIG. 3 shows an embodiment of the sensor section 70 for detecting a magnetic anisotropy of an object 40 to be inspected. A DC magnet 10 and a small-sized AC magnet 12 are wound around a horseshoe-shaped yoke 13. A magnetic sensor 11a is placed in a central portion of the yoke 13 to measure a leakage magnetic field from the object (or pipe) 40. A magnetic sensor 11b is placed at one end of the yoke 13 to measure a direct magnetic field from the object 40. The yoke 13, the DC magnet 10, the small-sized AC magnet 12 and the magnetic sensors 11a and 11b are integrated by a sensor holder 100.

Figure 4:
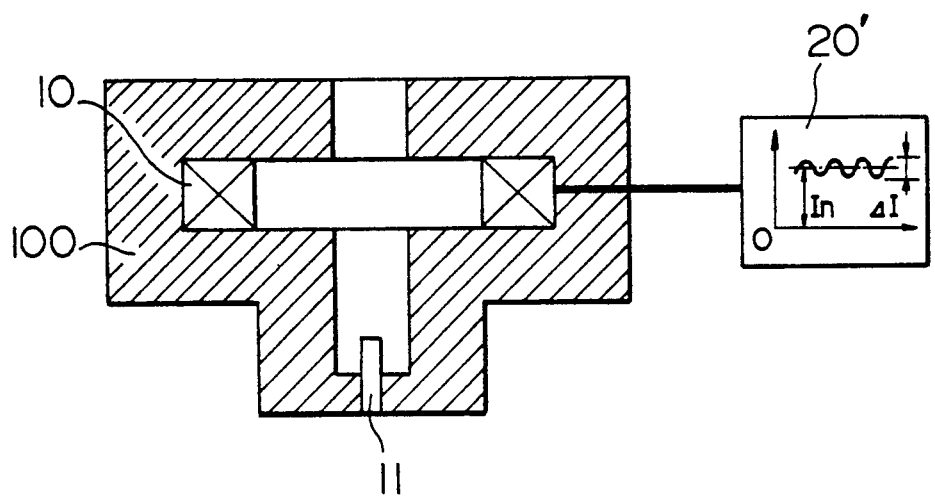
FIG. 4 is a detailed cross section showing a third embodiment of the sensor section shown in FIG. 1.

FIG. 4 is a detailed cross section of a third embodiment of the sensor section 70 shown in FIG. 1. More especially, FIG. 4 shows an embodiment of the sensor section 70 in which the sensor section is composed of a DC magnet 10 and a magnetic sensor 11, and a magnetizing power source 20' having a function of providing the superposition of a DC component and a small AC component as a magnetizing current to be applied to the DC magnet 10 is connected to the DC magnet 10. In other words, the magnetizing power source 20' is substituted for the DC power source 20 and the AC power source 22 shown in FIG. 1 or has a function equivalent to the function of adding a small AC component of the AC power source 22 to the DC power source 20 of the DC magnet 10. According to the present embodiment, the small-sized AC magnet 12 can be removed. The DC magnet 10 and the magnetic sensor 11 are integrated by a sensor holder 100.

Figure 5A:
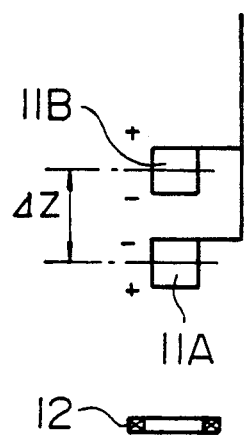
FIG. 5A shows the detailed layout of an embodiment of a magnetic sensor used in the sensor section shown in FIGS. 2 to 4.
Figure 5B:
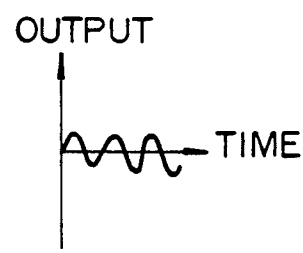
FIG. 5B shows an output waveform of the magnetic sensor shown in FIG. 5A.

FIGS. 5A and 5B show the detailed layout and the output waveform of an embodiment of the magnetic sensor(s) 11 or 11a and 11b shown in FIGS. 2 to 4. More especially, FIGS. 5A and 5B show an embodiment of a differential type magnetic sensor 11 in which magnetic sensors 11A and 11B are arranged with an interval $\Delta Z$ therebetween in a direction of Z axis. In the case where a small AC magnetic field of the small-sized AC magnet 12 is to be detected in a state in which a DC magnetic field of the DC magnet 10 is applied, an output of the magnetic sensor 11 becomes large owing to the DC or base magnetic field so that it is hard to obtain a small AC output. Therefore, the two magnetic sensors 11A and 11B are connected in reverse directions so that only an AC component can be detected as a difference between outputs of the sensors 11A and 11B. As a result, an AC output waveform of the magnetic sensor 11 as shown in FIG. 5B is obtained.

Figure 6A:
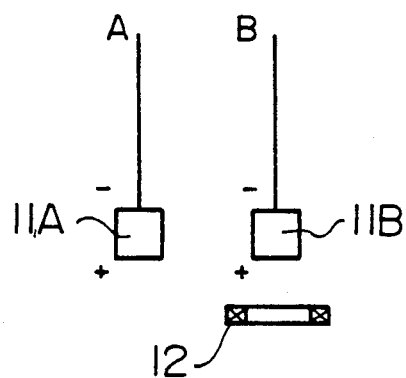
FIG. 6A shows the detailed layout of another embodiment of a magnetic sensor used in the sensor section shown in FIGS. 2 to 4.
Figure 6B:
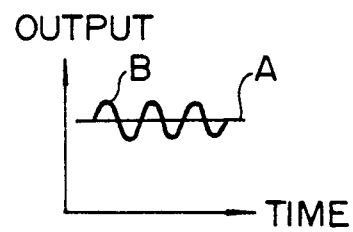
FIG. 6B shows an output waveform of the magnetic sensor shown in FIG. 6A.

FIGS. 6A and 6B show the detailed layout and the output waveform of another embodiment of the magnetic sensor(s) 11 or 11a and 11b shown in FIGS. 2 to 4. In FIGS. 6A and 6B, two magnetic sensors 11A and 11B are arranged so that a DC magnetic field and an AC magnetic field of the small-sized AC magnet 12 are measured by one 11A of the two magnetic sensors. An AC component is detected from a difference between output waveforms B and A of the two magnetic sensors 11B and 11A as shown in FIG. 6B.

Figure 7:
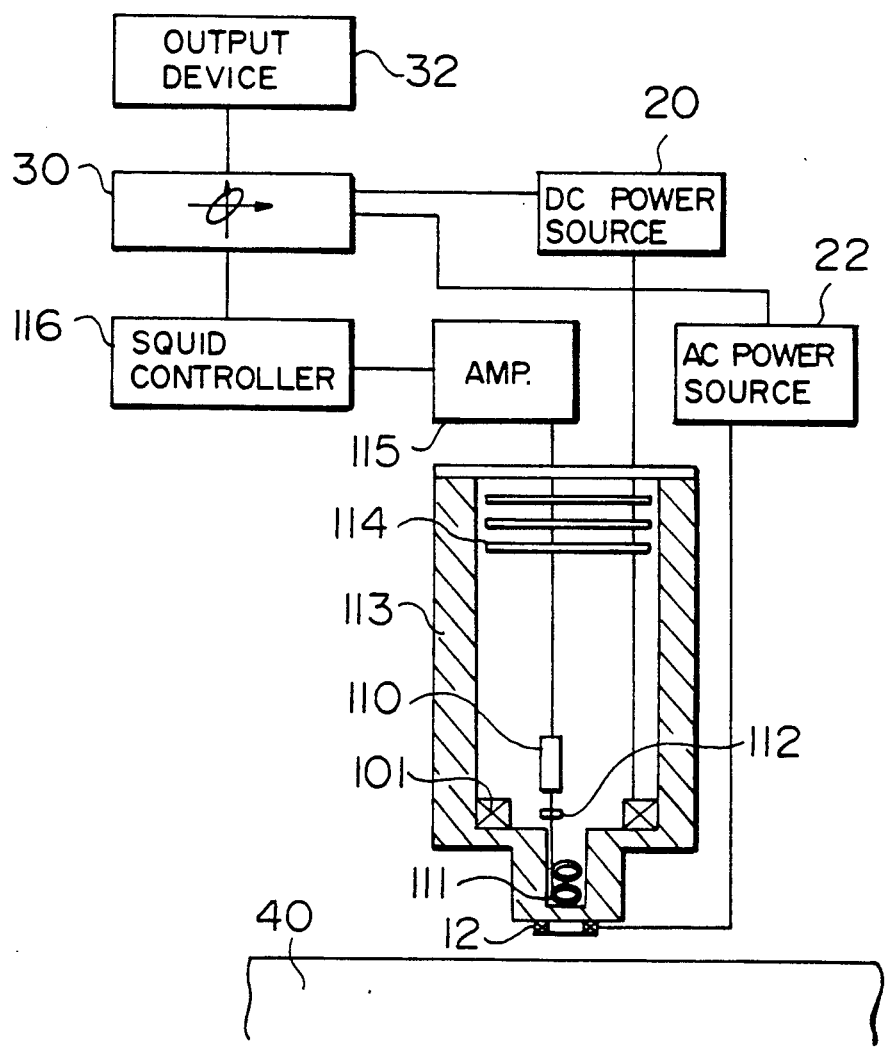
FIG. 7 is a detailed cross section showing a fourth embodiment of the sensor section shown in FIG. 1.

FIG. 7 is a detailed cross section of a fourth embodiment of the sensor section 70 shown in FIG. 1. More especially, FIG. 7 shows an embodiment of the sensor section 70 which uses a SQUID sensor system and a superconducting magnet. A cryostat 113 is filled with liquid helium and is cooled at 4.2° K. A SQUID 110, a pickup coil 111 and a superconducting magnet 101 are included in the cryostat 113. The pickup coil 111 to detect a magnetic field is connected to the SQUID 110 and the quantity of magnetism is converted into an electric signal by the SQUID 110 so that it can be detected with a high sensitivity of $2.07 \times 10^{-15}$ Wb. An output of the SQUID 110 is amplified by an amplifier 115 and is then processed by a SQUID controller 116. A heat switch 112 is provided between the pickup coil 111 and the SQUID 110. Upon change of a magnetic field of the superconducting magnet 101, the heat switch 112 is turned off to prevent a magnetic field from entering the SQUID 110, thereby protecting the SQUID 110. A small-sized AC normal-conducting magnet 12 for applying an AC magnetic field is arranged below the cryostat 113. The magnet 12 is made of a normal-conducting material such as copper. A stable DC magnetic field is applied to an object 40 by the superconducting magnet 101 and an AC magnetic field by the small-sized AC magnet 12 is detected by the SQUID sensor 110 with a high sensitivity. A thermal shield 114 for preventing the evaporation of liquid helium is arranged at an upper portion in the cryostat 113.

Figure 8:
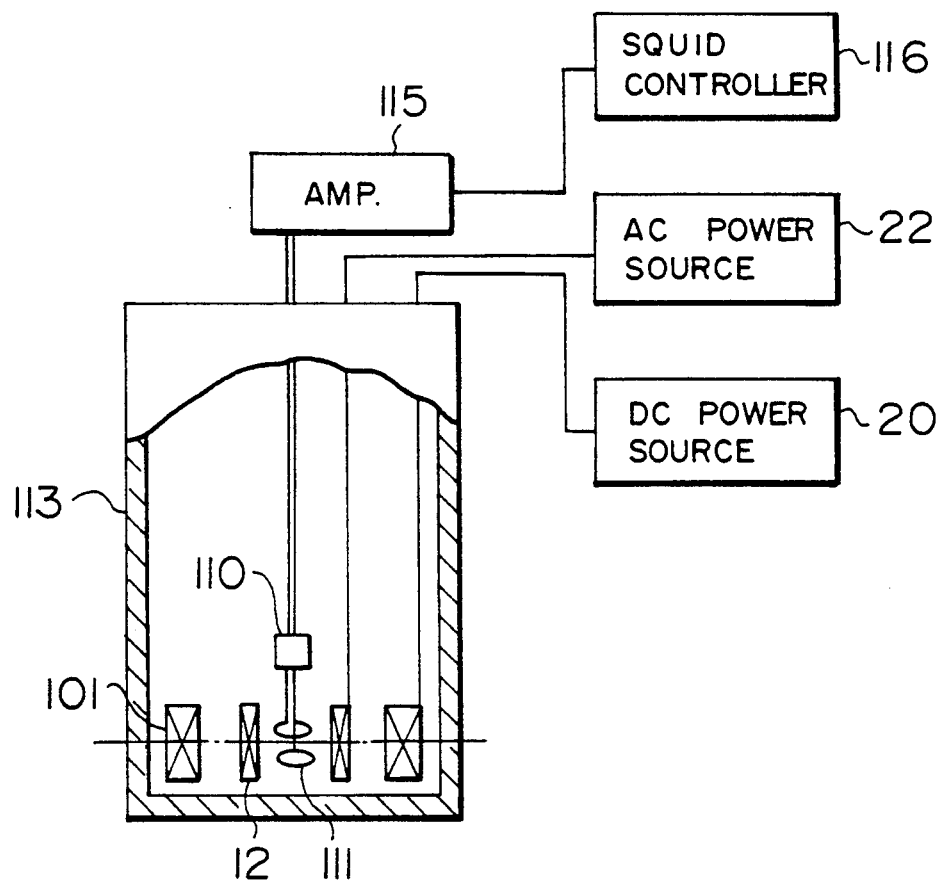
FIG. 8 is a detailed cross section showing a fifth embodiment of the sensor section shown in FIG. 1.

FIG. 8 is a detailed cross section of a fifth embodiment of the sensor section 70 shown in FIG. 1. More especially, FIG. 8 shows an embodiment in which in conjunction with the sensor section with SQUID sensor shown in FIG. 7, the layout or arrangement of a superconducting magnet 101, an AC magnet 12 and a magnetism detecting pickup coil 111 is restricted. Usually, a differential coil is used for the pickup coil 111 shown in FIG. 8, in order to cancel external magnetic field noises and magnetic fields of the magnets upon magnetization. Accordingly, in order to detect only a change in magnetic field caused by the material of the object 40 to be inspected, the pickup coil 111 is placed at a position x where a change $$\frac{\partial B}{\partial x}$$

in magnetic flux density B becomes 0 in the magnetic fields generated by the superconducting magnet 101 and the AC magnet 12.

Figure 9:
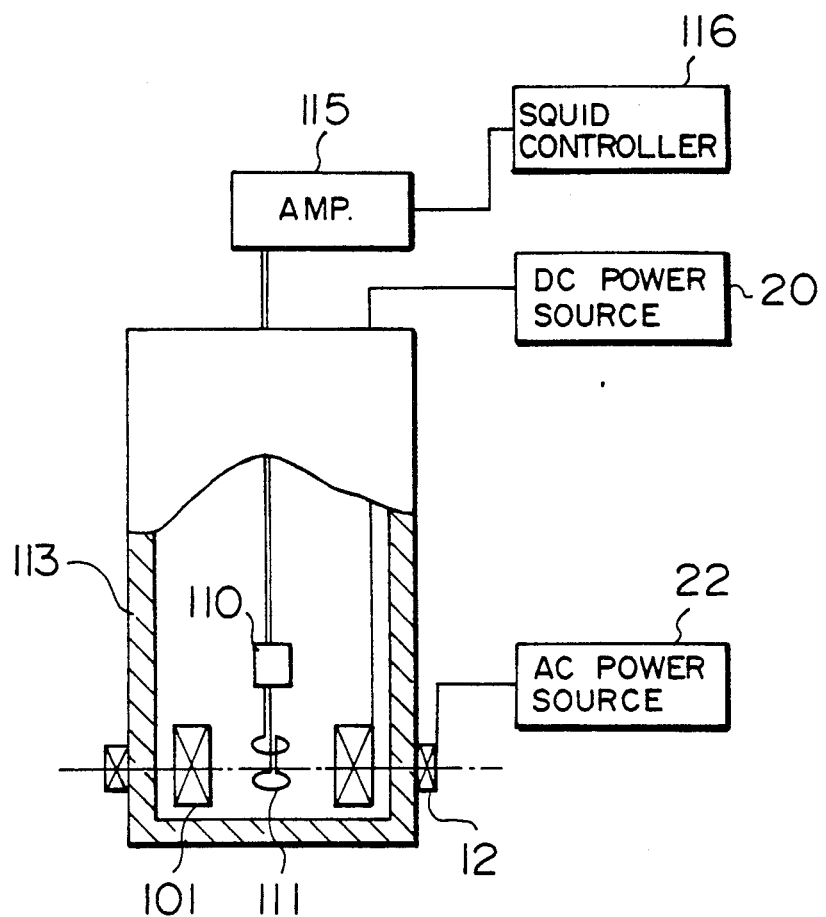
FIG. 9 is a detailed cross section showing a sixth embodiment of the sensor section shown in FIG. 1.

FIG. 9 is a detailed cross section of a sixth embodiment of the sensor section 70 shown in FIG. 1. More especially, FIG. 9 shows an embodiment in which in conjunction with the sensor section with SQUID sensor shown in FIG. 7 or 8, an AC normal-conducting magnet 12 which is easy to apply an AC magnetic field, is arranged outside of a superconducting magnet 101.

Figure 10:
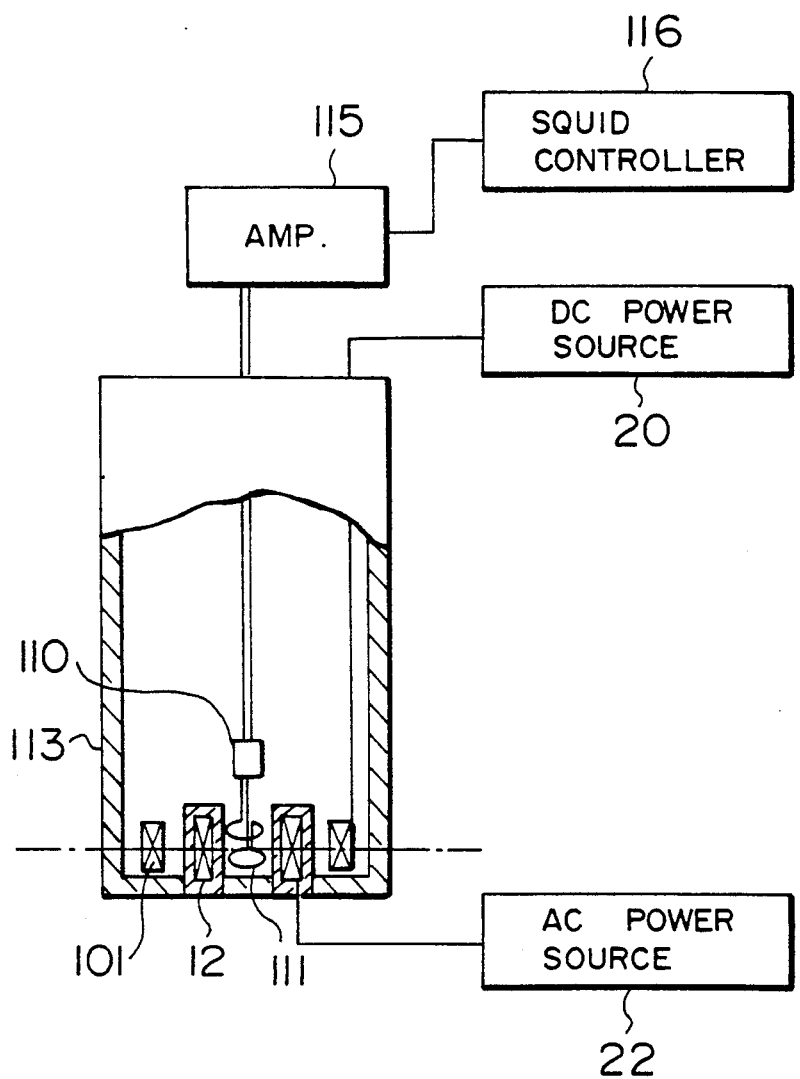
FIG. 10 is a detailed cross section showing a seventh embodiment of the sensor section shown in FIG. 1.

FIG. 10 is a detailed cross section of a seventh embodiment of the sensor section 70 shown in FIG. 1. More especially, FIG. 10 shows an embodiment in which in conjunction with the sensor section with SQUID sensor shown in FIG. 7 or 8, an AC normal-conducting magnet 12 is arranged inside of a superconducting magnet 101 in opposition to the embodiment shown in FIG. 9.

Recently, a high-temperature superconducting material to operate at a liquid nitrogen temperature has been developed. If a high-temperature SQUID utilizing this high-temperature superconducting can be realized, it can be used in the embodiments the sensor section 70 of FIGS. 7 to 10 using the SQUID sensor system and the superconducting magnet. In this case, the size of the SQUID sensor can be made small since it is possible to use liquid nitrogen for cooling.

Figure 11A:
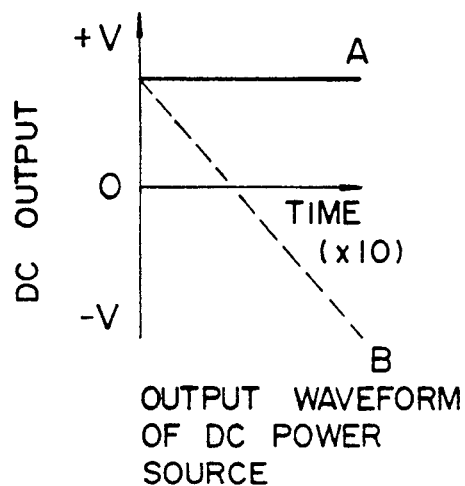
FIGS. 11A and 11B show as a whole an embodiment of output waveforms of a DC power source and an AC power source shown in FIGS. 1 and 7 to 10.
Figure 11B:
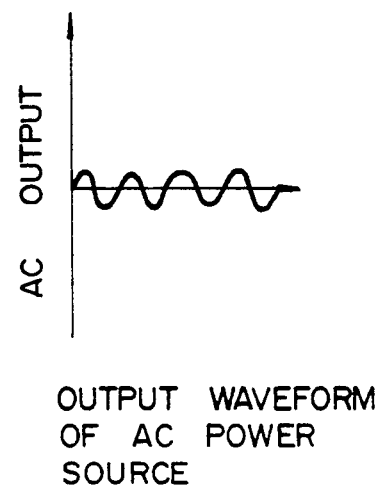

FIGS. 11A and 11B show as a whole an embodiment of output waveforms of the DC power source 20 and the AC power source 22 shown in FIGS. 1 and 7 to 10. As shown in FIG. 11A, a DC output waveform of the DC power source 20 may take either a waveform A which provides a constant output or a waveform B which changes at a period much longer than that of an AC output waveform of the AC power source 22 shown in FIG. 11B. In the case of the waveform A, a small hysteresis is measured by means of the AC output with the DC output being step-wise changed. In the case of the waveform B, the measurement is made continuously.

Figure 12A:
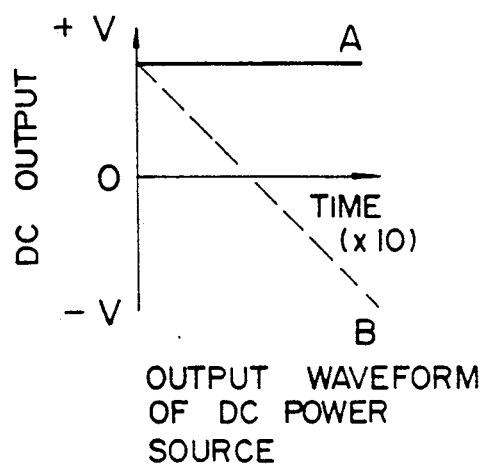
FIGS. 12A and 12B show as a whole another embodiment of output waveforms of the DC power source and the AC power source shown in FIGS. 1 and 7 to 10.
Figure 12B:
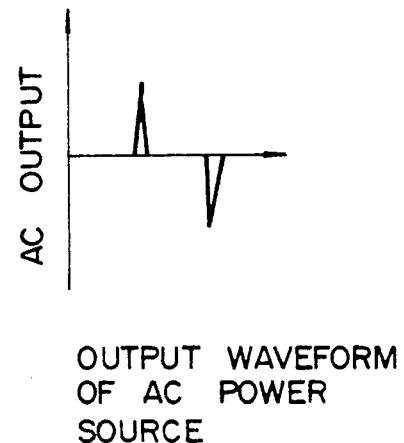

FIGS. 12A and 12B show as a whole another embodiment of output waveforms of the DC power source 20 and the AC power source 22 shown in FIGS. 1 and 7 to 10. As shown in FIG. 12A, a DC output waveform of the DC power source 20 may take either a waveform A or a waveform B, like the embodiment shown in FIGS. 11A and 11B. An AC output waveform of the AC power source 22 has a pulse-like waveform, as shown in FIG. 12B. The pulse-like AC output is used to detect damages in the material of the object 40 from a sudden change of a magnetic characteristic (or magnetic domain) and to use in combination the AC magnet 12 and the DC magnet 10 or 101. According to the present embodiment, it is also possible to detect a small change of a magnetic domain such as Barkhausen noises.

Next, the magnetic measurement and degradation/damage decision method for the weld zone 41 of the object 40 or the like in the embodiments shown in FIGS. 1 to 12 and the operation or procedure of the method will be explained by use of FIGS. 13 to 21.

Figure 13:
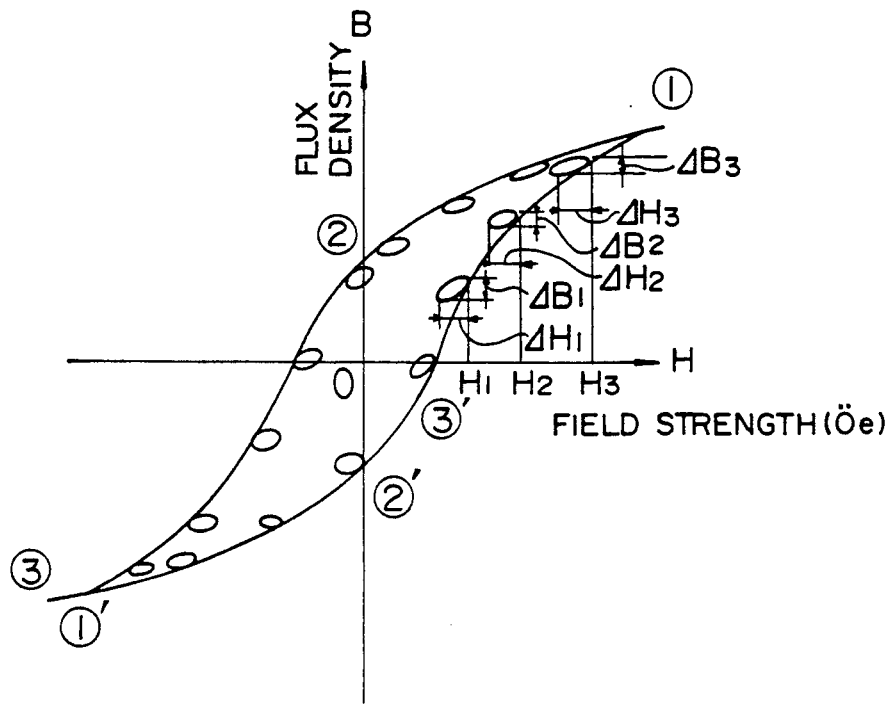
FIG. 13 shows the B-H curve of the metal material of an object to be inspected which is shown in FIG. 1.

FIG. 13 shows the magnetic hysteresis loop or B-H curve of the metal material of the object 40 shown in FIG. 1. Referring to FIG. 13, after the magnetization has been made through the course of ①'→②'→③' in the B-H curve, an AC magnetic field $\Delta H_1$ is applied when a DC magnetic field is $H_1$. Thereby, a magnetic flux density B changes by $\Delta B_1$. A $\Delta B_1$-$\Delta H_1$ curve at this time is as shown in FIG. 13. Next, the DC magnetic field is changed to $H_2$ to make a similar measurement. The above operation is repeated until ① (at a saturation magnetic field or magnetization) and further until ②→③ to conduct the measurement of $\Delta B$-$\Delta H$ curves through the application of the AC magnetic field with the DC magnetic field being changed.

Figure 14:
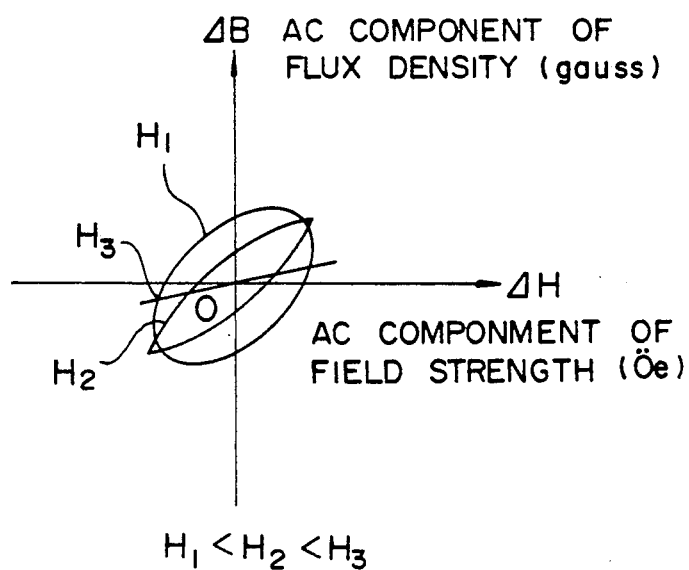
FIG. 14 shows $\Delta B$-$\Delta H$ curves at small magnetic regions of the B-H curve shown in FIG. 13.

FIG. 14 shows $\Delta B$-$\Delta H$ curves at small magnetized regions of the B-H curve shown in FIG. 13. FIG. 14 shows the $\Delta B$-$\Delta H$ curves obtained by the measurement method explained in conjunction with FIG. 13. From FIG. 14, it is seen that the $\Delta B$-$\Delta H$ curve changes depending on the DC magnetic field $H_i$ (i=1, 2, 3, —). The pattern of $\Delta B$-$\Delta H$ curve depends on the degree of thermal aging (or age degradation) or strain damage of the material of the object 40 .

Figure 15:
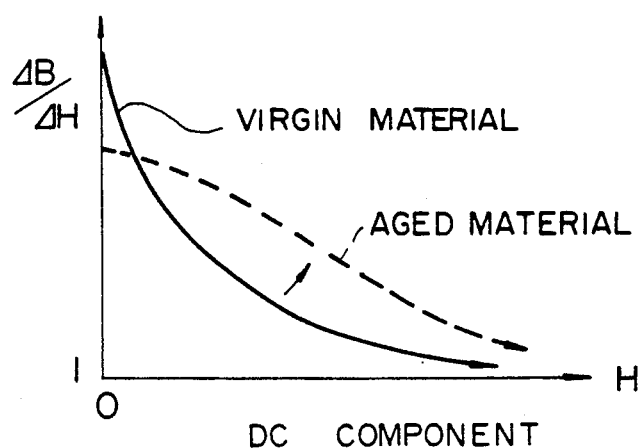
FIG. 15 shows an example of the result of measurement of a relationship between $\Delta B/\Delta H$ and H for a virgin metal material and an aged metal material of the object shown in FIG. 1.

FIG. 15 shows an example of the result of measurement of a relationship between $\Delta B/\Delta H$ and DC magnetic field component H for a virgin metal material and an aged (or degraded) metal material of the object 40 shown in FIG. 1. A change pattern of $\Delta B/\Delta H$-H is different depending on the degree of age degradation of the material of the object 40, as shown in FIG. 15. Therefore, this measurement data can be used as master curves of a data base.

Figure 16:
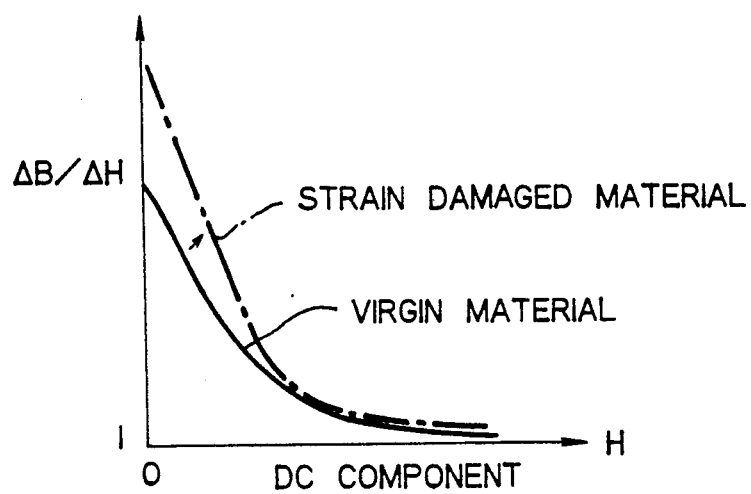
FIG. 16 shows an example of the result of measurement of a relationship between $\Delta B/\Delta H$ and H for a virgin metal material and a strain-damaged metal material of the object shown in FIG. 1.

FIG. 16 shows an example of the result of measurement of a relationship between $\Delta B/\Delta H$ and DC magnetic field component H for a virgin metal material and a strain-damaged metal material of the object 40 shown in FIG. 1. As seen from FIG. 16, a change pattern of $\Delta B/\Delta H$-H is different depending on the degree of strain damage of the material of the object 40. Therefore, this measurement data can be used as master curves of a data base.

Figure 17:
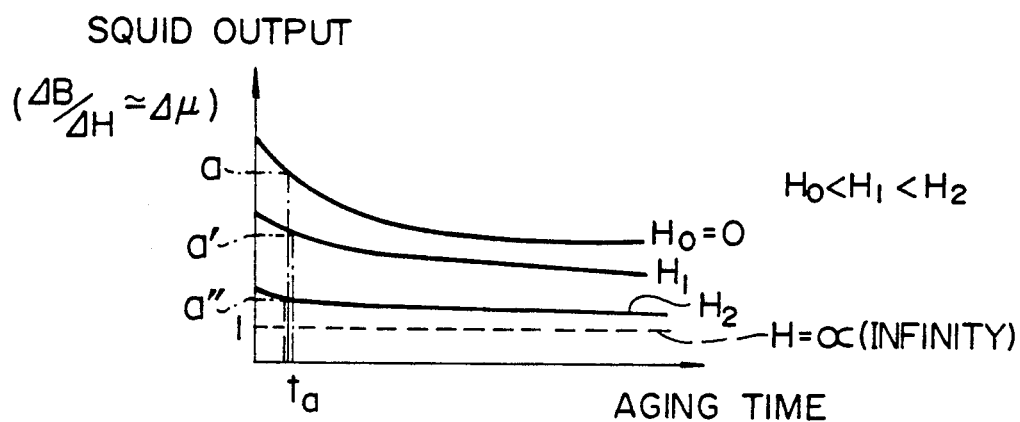
FIG. 17 shows an example of the result of measurement of a relationship between aging time and SQUID output for the metal material of the object shown in FIG. 1 when H is taken a parameter.

FIG. 17 shows an example of the result of measurement of a relationship between aging time and SQUID output ($\Delta B/\Delta H \simeq \Delta\mu$) for the metal material of the object 40 of FIG. 1 by the sensor section 70 using the SQUID sensor and the superconducting magnet when a DC magnetic field H is taken as a parameter. As shown in FIG. 17, the output ($\Delta B/\Delta H \simeq \Delta\mu$) of the SQUID 110 decreases with the increase in aging time. Also, the larger the DC magnetic field $H_i$, the smaller the output ($\Delta B/\Delta H \simeq \Delta\mu$) of the SQUID 110.

Figure 18:
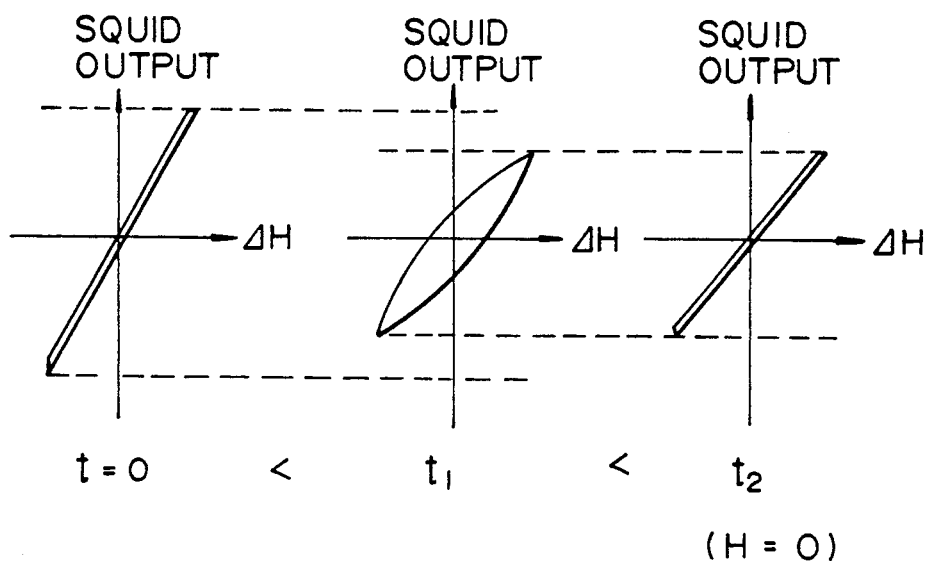
FIG. 18 shows an example of the result of measurement of a change of the $\Delta B$-$\Delta H$ curve depending on an aging time when H is 0 in FIG. 17.

FIG. 18 shows an example of the result of measurement of a change of the $\Delta B/\Delta H$ curve depending on an aging time when the DC magnetic field H is 0 in FIG. 17. The $\Delta B/\Delta H$ curve as the SQUID output when H=0 changes with the increase in aging time $t=0<t_1<t_2$, as shown in FIG. 18.

Figure 19:
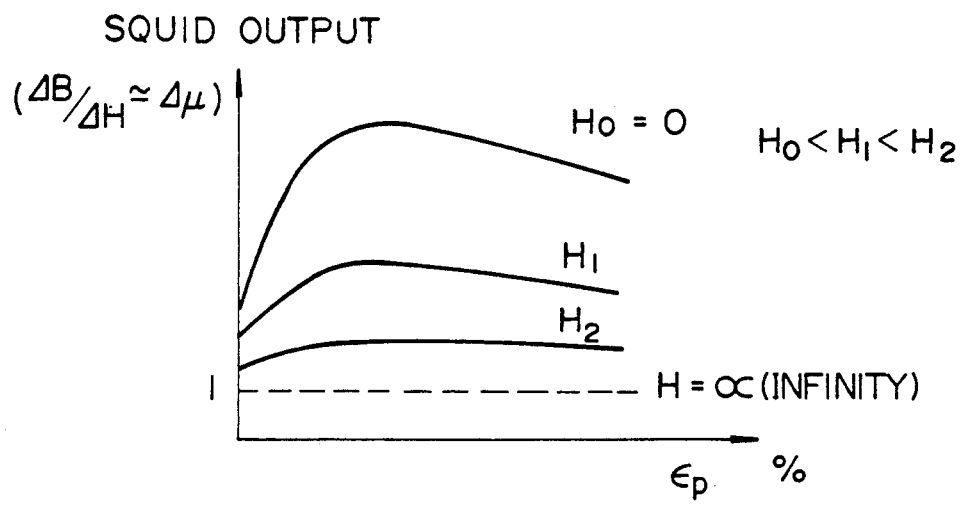
FIG. 19 shows an example of the result of measurement of a relationship between strain quantity and SQUID output for the metal material of the object shown in FIG. 1 when H is taken as a parameter.

FIG. 19 shows an example of the result of measurement of a relationship between load strain quantity $\epsilon_p$ (%) of strain damage and SQUID output for the metal material of the object 40 of FIG. 1 by the sensor section 70 using the SQUID sensor and the superconducting magnet when the DC magnetic field H is taken as a parameter. As shown in FIG. 19, the output ($\Delta B/\Delta H \simeq \Delta\mu$) of the SQUID 110 increases and thereafter decreases with the increase in load strain quantity $\epsilon_p$ (%). Also, the larger the DC magnetic field $H_i$, the smaller the output ($\Delta B/\Delta H \simeq \Delta\mu$) of the SQUID 110.

Figure 20:
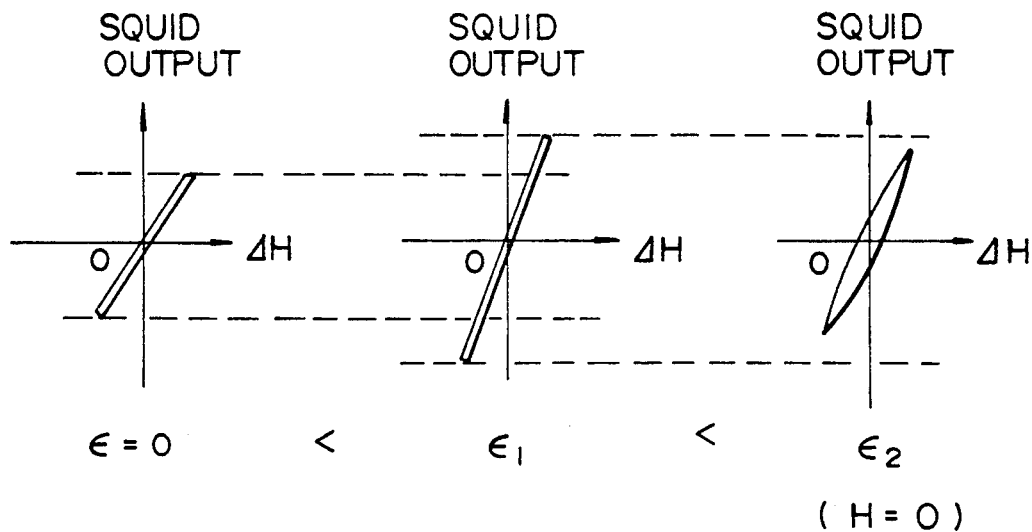
FIG. 20 shows an example of the result of measurement of a change of the $\Delta B$-$\Delta H$ curve depending on the strain quantity $\epsilon_p$ when H is 0 in FIG. 19.

FIG. 20 shows an example of the result of measurement of a change of the $\Delta B$-$\Delta H$ curve depending on the load strain quantity $\epsilon_p$ when the DC magnetic field H is 0 in FIG. 19. The $\Delta B$-$\Delta H$ curve as the SQUID output when H=0 changes with the increase in load strain quantity $\epsilon_p=0<\epsilon_1<\epsilon_2$, as shown in FIG. 20.

If the measurement data shown in FIGS. 17 to 20 is used as master curves of the data base and $\Delta B$-$\Delta H$ curves to which reference is to be made for comparison, the degree of age degradation and/or the degree of strain damage for the metal material of the object 40 can be decided by performing a comparison operation on the actually measured data of the object 40.

Figure 21:
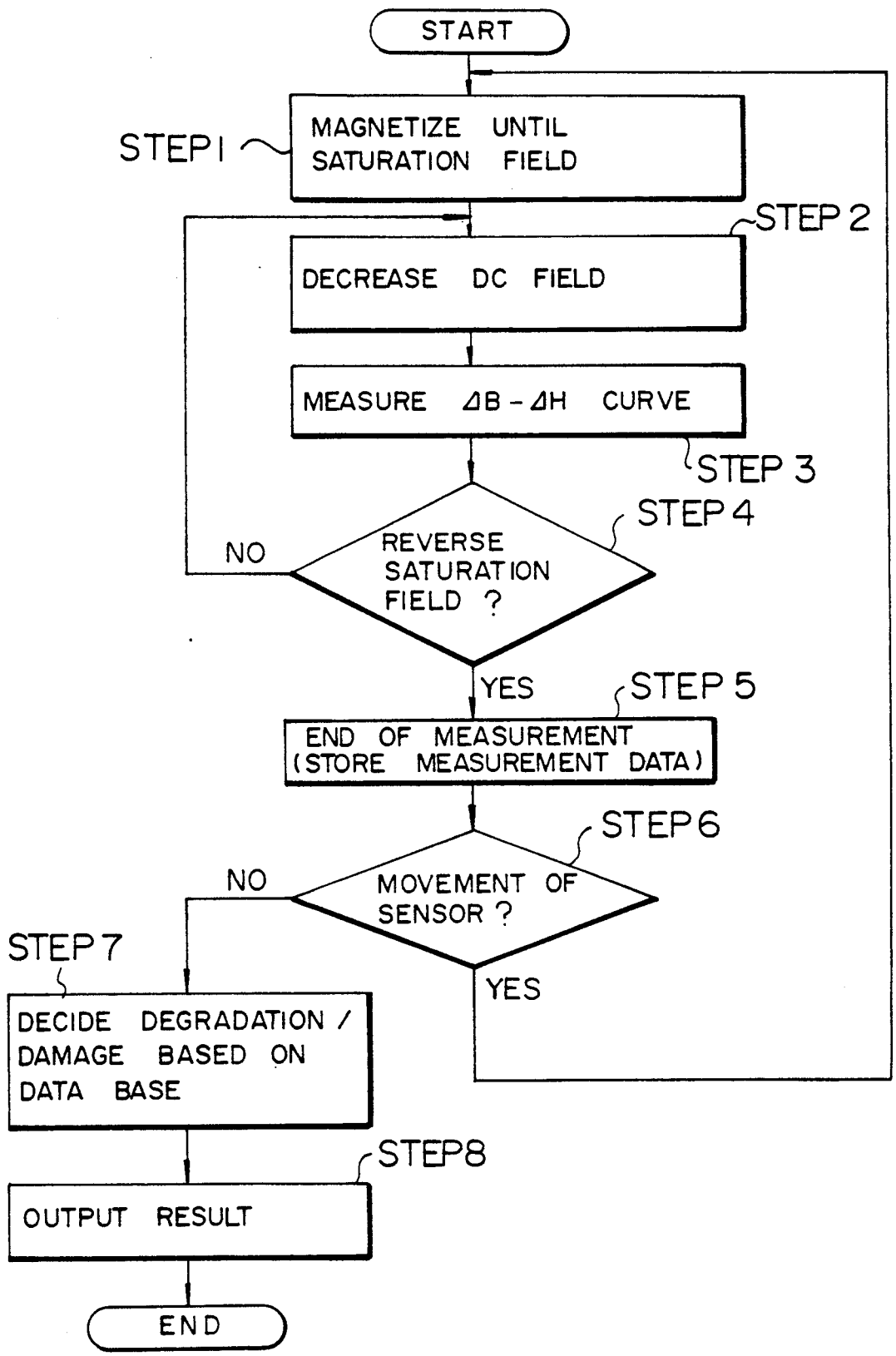
FIG. 21 is a flow chart showing an example of a procedure for magnetic measurement and degradation/damage decision for the object in the embodiments shown in FIGS. 1 to 12.

FIG. 21 is a flow chart showing an example of a procedure for magnetic measurement and degradation/damage decision for the weld zone 41 of the object 40 in the embodiments shown in FIGS. 1 to 12. Referring to FIG. 21, after an apparatus as shown in FIG. 1 has been set for the object (or pipe) 40, a region of the weld zone 41 to be inspected is magnetized until a saturation magnetic field of the B-H curve of FIG. 13 to remove a magnetic hysteresis (step 1). Next, in step 2, the DC magnetic field of the DC magnet 10 or 101 is decreased to a value $H_i$ at which measurement is to be made. In step 3, such a $\Delta B$-$\Delta H$ curve by the AC magnet 12 as shown in FIG. 13 is measured by the magnetic sensor 11 or 110 of the sensor section 70. The operation of steps 2 and 3 is repeated until a reverse saturation magnetic field or magnetism is reached. In the case where the decision as being the reverse saturation magnetic field is made in step 4, the process goes to step 5 in which measurement data of $\Delta B$-$\Delta H$ curves under the DC magnetic fields $H_i$ (i=1, 2, 3, —) is stored into a memory. Thereafter, in step 6, the sensor section 70 is moved to make measurement again starting from step 1. When the inspection at all measuring positions is completed (step 6), the process goes to step 7 in which the decision of degradation/damage based on the data base obtained from FIGS. 15 to 20 is made. Subsequently, in step 8, the result of degradation/damage decision is displayed on the display 31 and/or outputted by the output device 32.

According to the foregoing embodiments, it is possible to detect the degree of degradation and/or the degree of damage of a metal material by measuring a change of the $\Delta B$-$\Delta H$ curve by a small AC magnetic field accompanying a DC magnetic field. Also, even in the case where an AC magnetic field is small, measurement with a high precision is possible by use of a differential type magnetic sensor. Especially, in the case where a SQUID sensor is used, detection can be made in a non-contact manner.

Next, embodiments of a non-destructive defect inspection apparatus according to the present invention will be explained.

Figure 22:
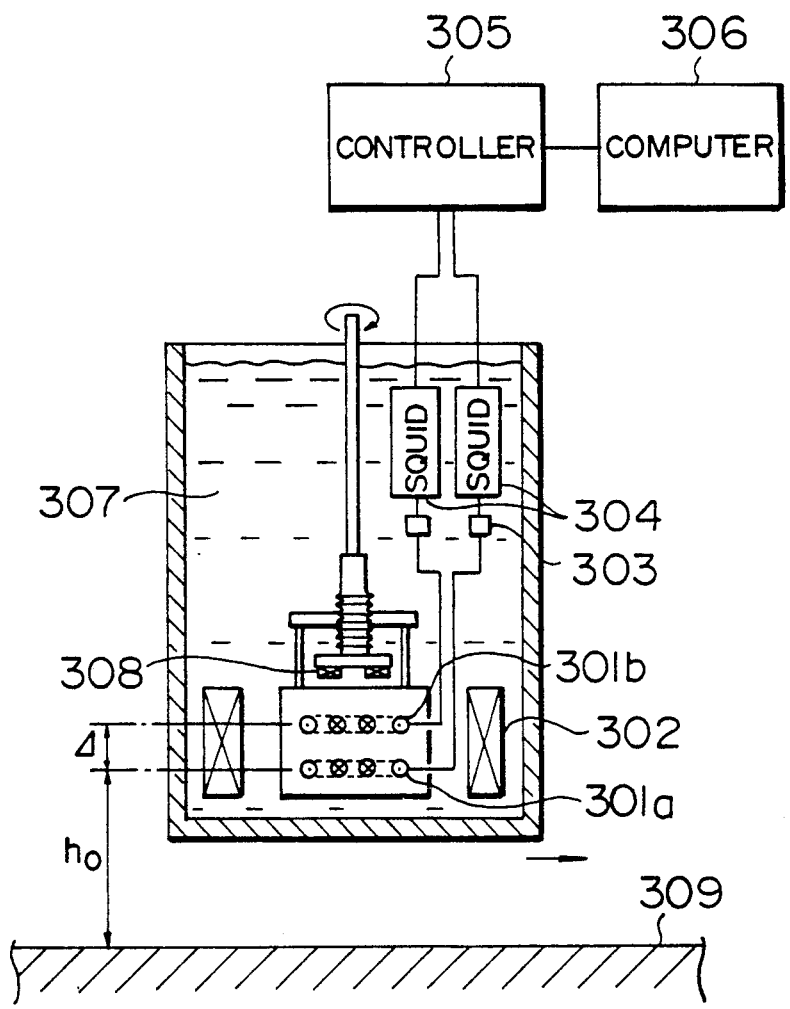
FIG. 22 is a view showing the construction of an embodiment of a non-destructive defect inspection apparatus according to the present embodiment.

FIG. 22 shows the construction of an embodiment of the present invention in which two pickup coils are used in non-destructive defect inspection magnetometry. A non-destructive inspection SQUID magnetometer apparatus according to the present embodiment includes two pickup coils 301 (301a and 301b), a magnetizing coil 302, SQUID's 304 connected to the pickup coils 301 through heat switches 303, a controller 305 for controlling the SQUID's 304 and measuring outputs of the SQUID's, a computer 306 for performing a processing for analysis of and operation on the SQUID outputs, a cooling medium 307 for producing a superconducting condition, and a balance ring 308 for balancing the initial outputs of the SQUID's. The two pickup coils 301a and 301b are provided at different distances from the surface 309 of an object to be inspected.

Figure 23:
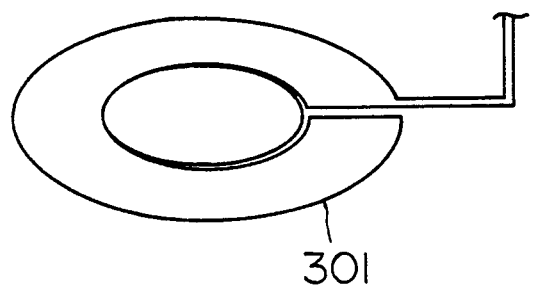
FIG. 23 is a perspective view showing the structure of a pickup coil.

FIG. 23 shows the details of the pickup coil (or gradiometer) 301. Outer and inner portions of the coil have different directions of winding.

Figure 24:
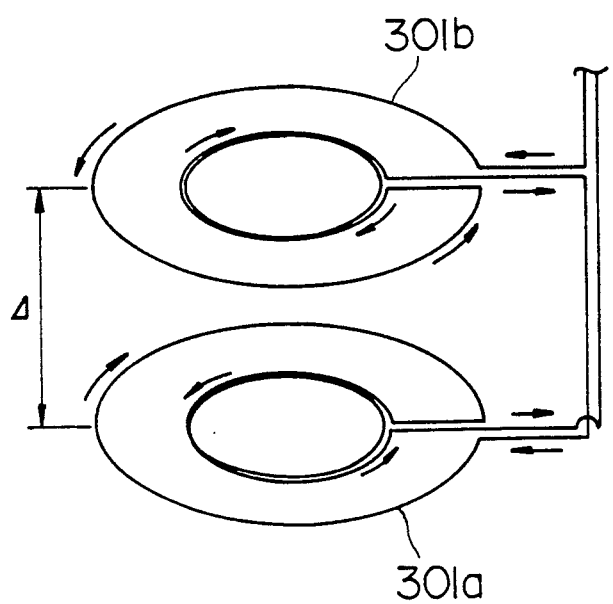
FIG. 24 is a perspective view showing a relationship between two pickup coils.
Figure 25:
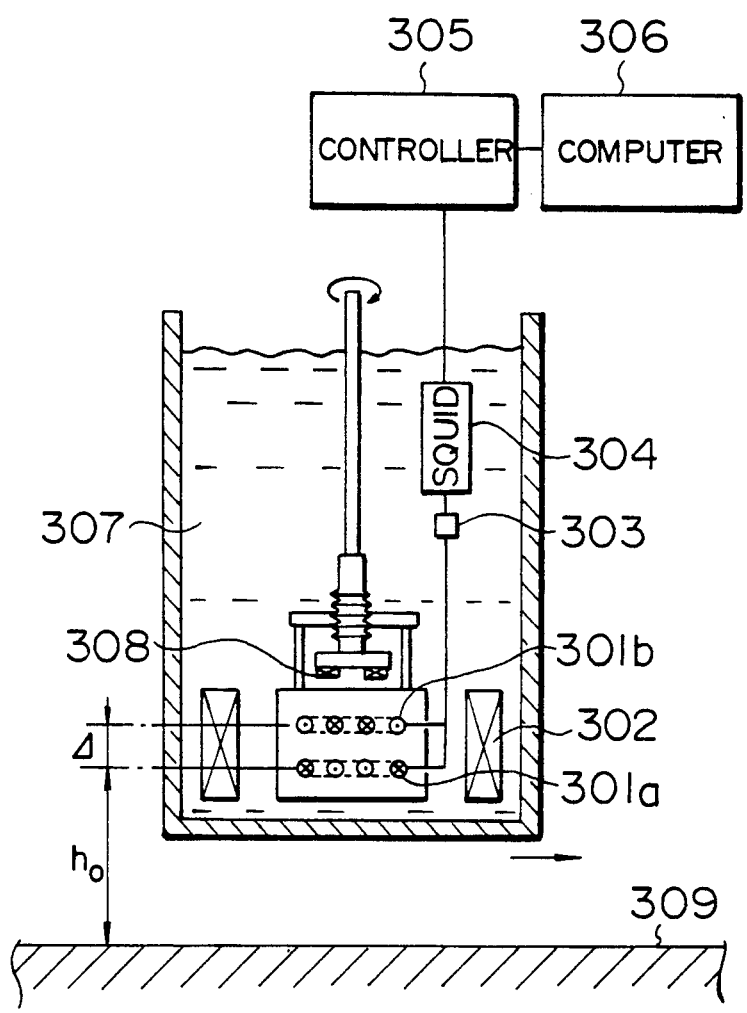
FIG. 25 is a view showing an example of the construction of an apparatus using the pickup coils shown in FIG. 24.

FIG. 24 shows an example in which two pickup coils are connected to provide a sensor, and FIG. 25 schematically shows the construction of an apparatus which uses the pickup coils shown in FIG. 24. In FIG. 24, the directions of winding of the two pickup coils 301a and 301b are reverse to each other. When a magnetic force is exerted on this sensor, the directions of currents generated in the coils become reverse to each other. Accordingly, a difference between outputs of the two pickup coils becomes an output of the sensor body. In FIG. 25, this sensor output is amplified by a SQUID 304 through a heat switch 303.

With the above construction of the apparatus, it is possible to reduce a background signal depending on the geometry of the surface 309 of an object to be inspected.

In FIGS. 22 and 25, the interval A between the two pickup coils 301a and 301b and the initial distance $h_0$ between the surface 309 of the object and the pickup coil 301a are set to satisfy the condition of $20 \leq h_0 \leq 100$ mm and $2 \leq A \leq 10$ mm or the condition of 10

$\leq h_0/\Delta \leq 20$. This dimensional setting is experimentially determined on the basis of interference between pickup coils, sensitivity of pickup coil, and so on.

Figure 26A:
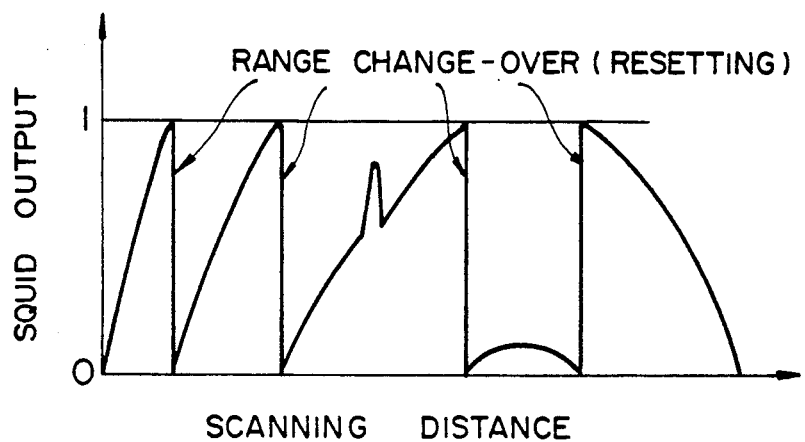
FIGS. 26A to 26C are views for explaining the measurement by the conventional apparatus.
Figure 26B:
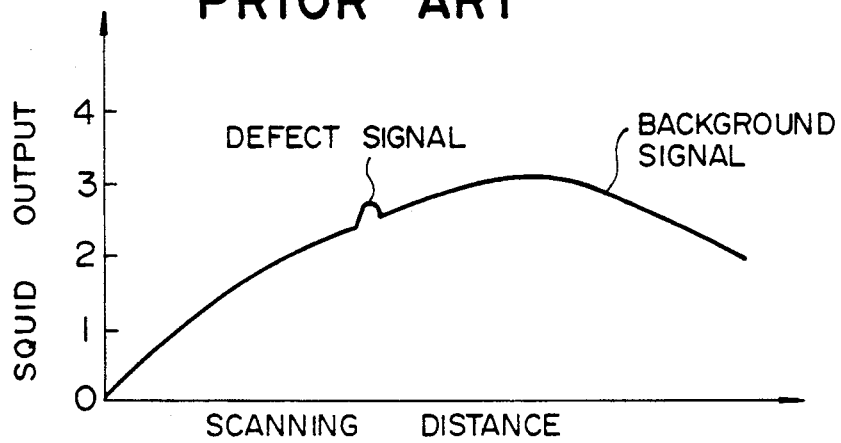
Figure 26C:
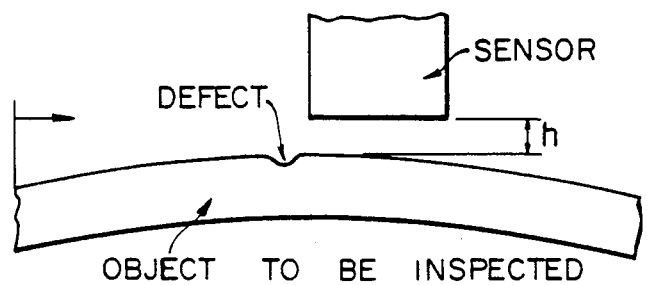

The outline of the defect measurement by the conventional non-destructive inspection SQUID magnetometer apparatus are shown in FIGS. 26A to 26C. In the case where a SQUID sensor is scanned on an object having a defect, as shown in FIG. 26C, an output of the SQUID is as shown in FIG. 26A. The SQUID must be reset by the change-over of the measuring range when its output exceeds a certain constant value (represented by 1 in FIG. 26A). The SQUID outputs in the ranges involved are combined or synthesized to obtain a composite output as shown in FIG. 26B. As seen from FIG. 26B, a background signal caused by the surface geometry of the object is considerably large. Therefore, it is necessary to reduce this background signal.

Figure 27A:
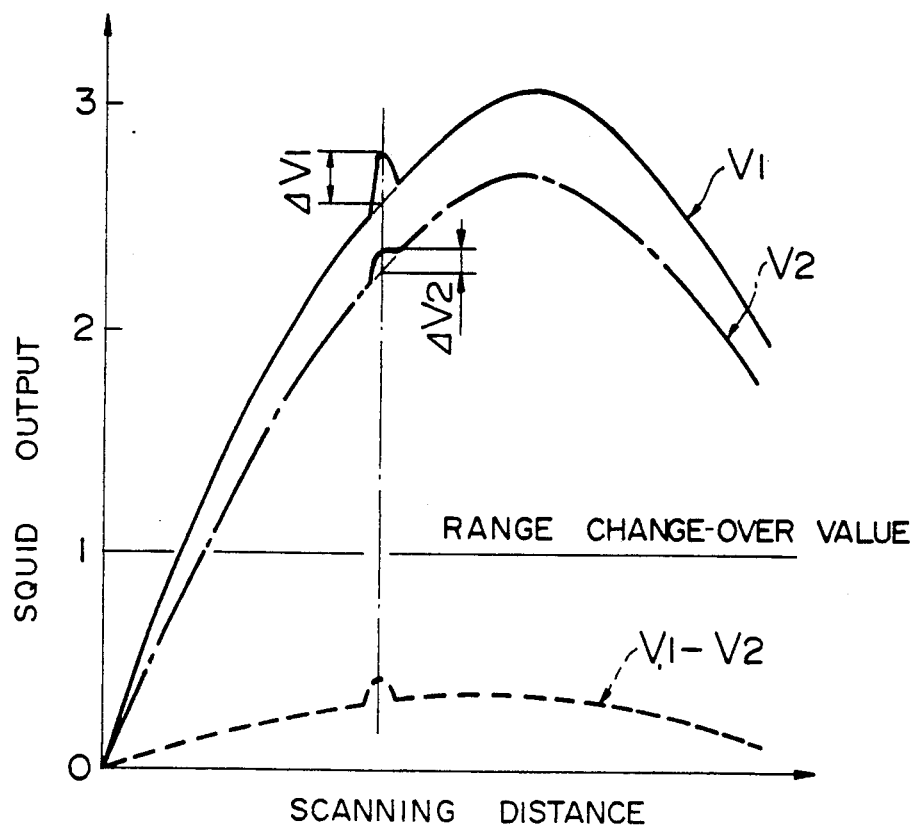
FIGS. 27A and 27B are views for explaining the measurement by the present invention.
Figure 27B:
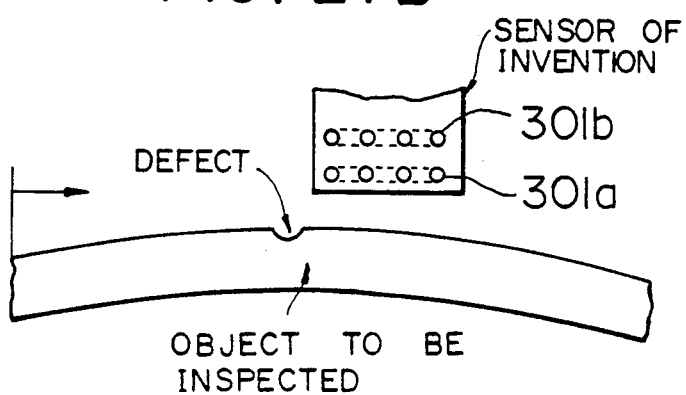

FIGS. 27A and 27B show the outline of the defect measurement by the present invention in the case where a SQUID is provided for each pickup coil, as shown in FIG. 22. SQUID outputs $V_1$ and $V_2$ are the outputs of the SQUID's connected to the pickup coils 301a and 301b. $V_1-V_2$ is a difference between both the SQUID outputs. Thereby, it is possible to greatly reduce a background signal.

Directing attention to defect signals $\Delta V_1$ and $\Delta V_2$ and taking equations (1), (2) and (3) into consideration, the ratio of $\Delta V_1$ to $\Delta V_2$ can be written as follows:

$$\frac{\Delta V_1}{\Delta V_2} = \left(\frac{h_0 + \Delta}{h_0}\right)^N \tag{14}$$

where N is an exponent. Equation (14) can be transformed as follows:

$$N = \frac{\log\left(\frac{\Delta V_1}{\Delta V_2}\right)}{\log\left(\frac{h_0 + \Delta}{h_0}\right)} \tag{15}$$

If $N \approx 1$, the decision as being a background signal depending on the surface geometry of an object to be inspected is made from equation (1). If $N \approx 3.5$, the decision as being a rectangular defect is made from equation (2). If $N \approx 5$, the decision as being a circular defect is made from equation (3). Accordingly, it is possible to determine the form of a defect by a single scan. Hence, it is possible to greatly shorten a defect form measurement time as compared with the conventional method in which the form of a defect is determined through plane-like scanning (or plural scans).

If the form of a defect is determined, it is possible to readily measure or determine the area of the deflect since a relationship between area of defect and SQUID output is experimentally known.

The above processing can be performed by the computer 306 shown in FIG. 22. Explanation of the case where three or more pickup coils are provided will be omitted but the measurement precision is improved with the increase in number of pickup coils.

In the case where pickup coils are connected as shown in FIG. 25, the output of a SQUID is equal to $V_1-V_2$ shown in FIG. 27A. In this case, it is not possible to determine the exponent N, as shown by equation (15), which determines the form of a defect. However, since the SQUID output is smaller than a value (represented by 1 in FIG. 27A) at which the range change-over is required, the range change-over is not needed during defect measurement. Accordingly, in this case, it is possible to remove a measurement error attendant upon the range change-over.

Figure 28:
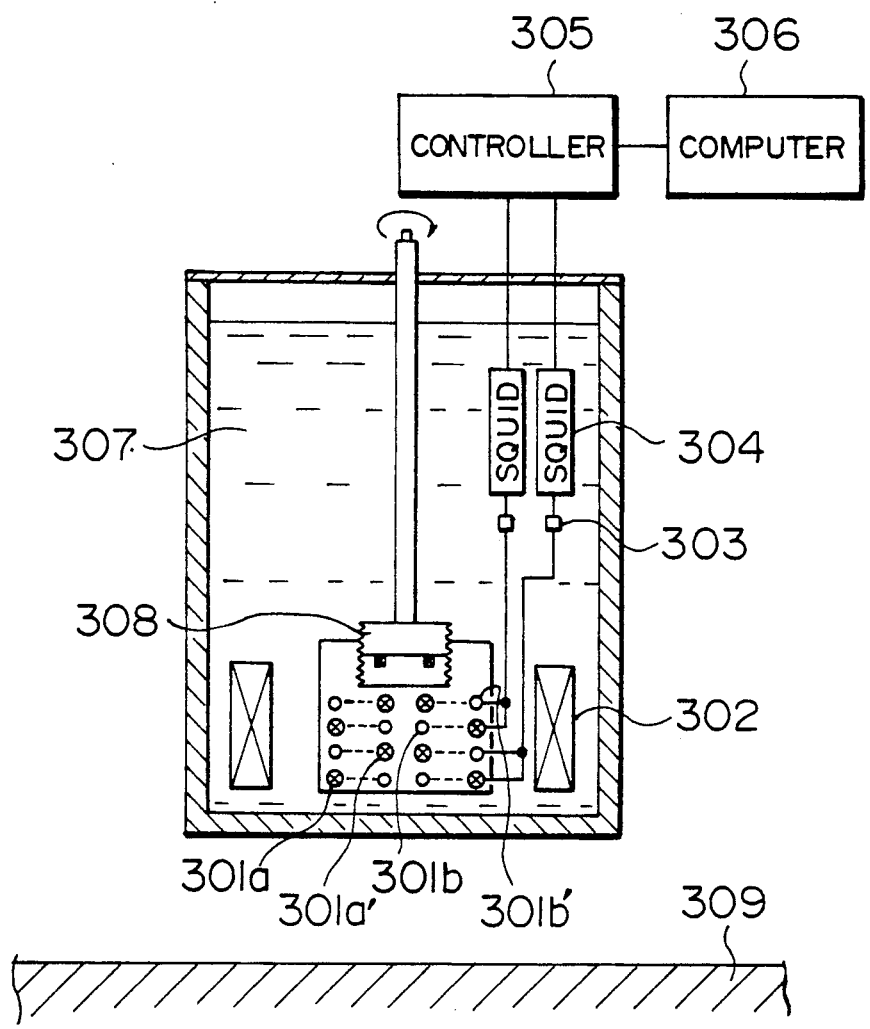
FIG. 28 is a view showing an example of the construction of an apparatus using a multiple pickup coil pair arrangement.
Figure 29:
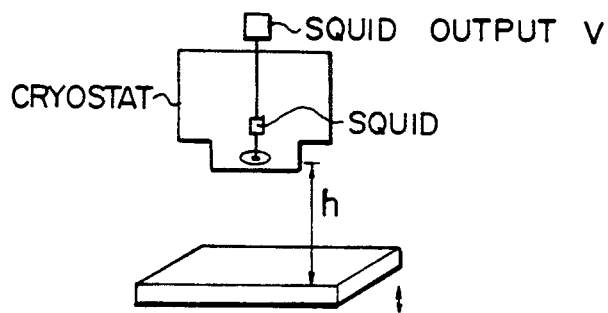
FIGS. 29 to 32 are views for explaining grounds for equations (1) to (3) concerning the present invention.
Figure 30:
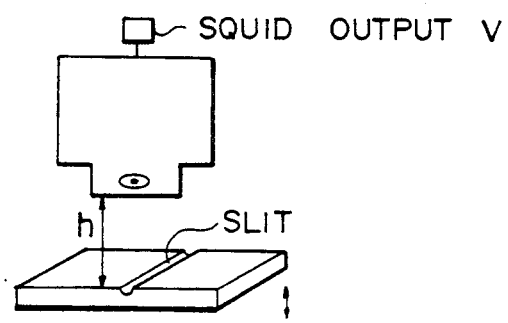
Figure 31:
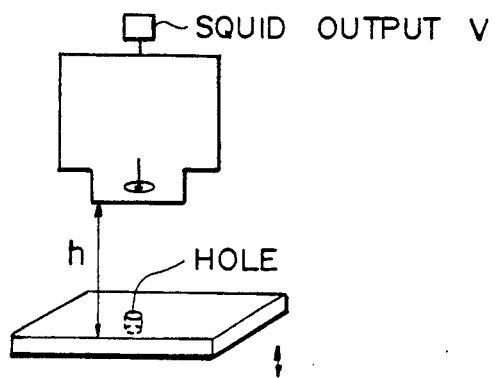
Figure 32:
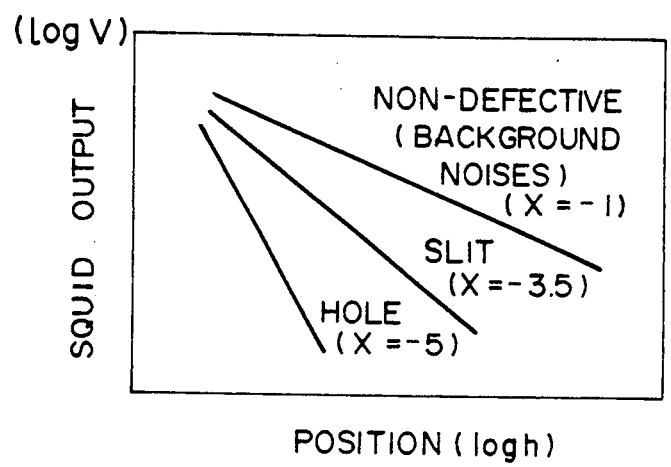

FIG. 28 shows an embodiment in which pickup coils taking the elimination of background noises into consideration are combined in a two-pair arrangement, thereby making it possible to decide the kind of a defect, too. More particularly, the present embodiment is constructed by two SQUID systems each of which has the same construction as that in FIG. 25. Background noises are reduced by each of a pair of pickup coils 301a and 301a' and a pair of pickup coils 301b and 301b'. The kind of a defect is decided by comparing a difference between outputs of the coils 301a and 301a' and a difference between outputs of the coils 301b and 301b'. According to the present embodiment, it is possible to detect a defect with a high precision since the background noises can be reduced and a defect signal can be amplified.

Figure 33:
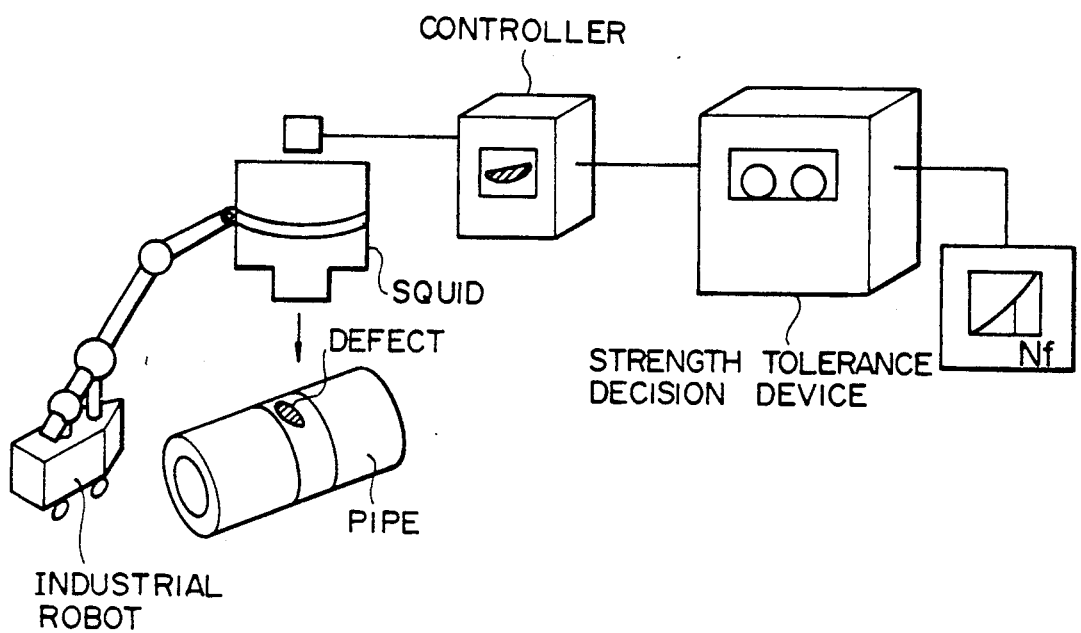
FIG. 33 is a view showing the construction of an embodiment in which a non-destructive inspection apparatus with SQUID is used in a strength tolerance decision system.

FIG. 33 shows an embodiment in which the above-mentioned non-destructive inspection apparatus with SQUID is used in a system for deciding the strength tolerance of an object to be inspected. In this system, a SQUID sensor is arranged at an end of a device for driving the inspection apparatus with SQUID, for example, a commercially available industrial articulated robot to measure or inspect an object such as a pipe. The system includes a decision device which performs an operation on the result of measurement by means of stress analysis or the like to decide or evaluate the strength tolerance of the pipe. According to the construction shown in FIG. 33, the evaluation of the strength of the object as well as the detection of a defect of the object are possible. As a result, the reliability is improved.

We claim:

1. An apparatus for inspecting degradation/damage of a material comprising:
   a DC magnet for applying a DC magnetic field to an object to be inspected so as to enable measurement of a magnetic hysteresis loop of said object;
   an AC magnet for applying a small AC magnetic field to said object to enable measurement of a minor magnetic hysteresis loop of said object;
   a magnetic sensor measuring said magnetic hysteresis loop and said minor magnetic hysteresis loop of said object; and
   a processing unit for detecting degradation/damage from measurement data of a magnetic characteristic of said object from said magnetic sensor and deciding the degree of degradation/damage;
   wherein said DC magnet includes a superconducting magnet and said magnetic sensor includes a SQUID sensor.

2. An apparatus according to claim 1, wherein said AC magnet is made of a normal-conducting material and is operated under a room-temperature environment outside of a cryostat.

3. An apparatus for inspecting degradation/damage of a material comprising:
   a DC magnet for applying a DC magnetic field to an object to be inspected so as to enable measurement of a magnetic hysteresis loop of said object;

an AC magnetic for applying a small AC magnetic field to said object to enable measurement of a minor magnetic hysteresis loop of said object;

a magnetic sensor measuring said magnetic hysteresis loop and said minor magnetic hysteresis loop of said object; and a processing unit for detecting degradation/damage from measurement data of a magnetic characteristic of said object form said magnetic sensor and deciding the degree of degradation/damage;

wherein said magnetic sensor is of a differential type and is placed at a position x where a change $$\frac{\partial B}{\partial x}$$

in magnetic flux density B becomes zero in the magnetic fields formed by said Dc magnet and said AC magnet, whereby it is possible to cancel components induced by a magnetic coil, thereby detecting only the magnetic characteristic of said object.

4. An apparatus for inspecting degradation/damage of a material comprising:

a superconducting magnet for applying a DC magnetic field to an object to be inspected so as to enable measurement of a magnetic hysteresis loop of said object;

an AC magnet for applying a changing magnetic field to said object to enable measurement of a minor magnetic hysteresis loop of said object;

a SQUID sensor for measuring said magnetic hysteresis loop and said minor magnetic hysteresis loop of said object;

a cryostat for cooling said superconducting magnet and said SQUID sensor; and a processing unit responsive to measurement data of a magnetic characteristic of said object from said SQUID sensor for deciding an abnormal value from said measurement data to detect the degradation/damage of said object.

5. An apparatus according to claim 4, wherein said superconducting magnet and said SQUID sensor are integrated.

6. An apparatus for inspecting damage of a material comprising a plurality of said pickup coils disposed at different distances from an object for detecting magnetic flux signals from said object, at least one said SQUID being connected to said plurality of pickup coils for receiving signals from said plurality of pickup coils and outputting SQUID output data, and a processing unit for receiving and processing said SQUID output data and for deciding a form of a defect of said object on the basis of a predetermined relationship among SQUID output data, distances between an object and pickup coils, and a defect form of an object.

7. An apparatus according to claim 4, wherein said processing unit determines the area of said defect from the decided form of said defect on the basis of a predetermined relationship between area of defect and SQUID output.

8. An apparatus according to claim 6, wherein a distance between said object and said pickup coils is set to be between 20 and 100 mm and an interval between said pickup coils is set to be between 2 and 10 mm.

9. An apparatus according to claim 6, wherein a distance h between said object and said pickup coils and an interval $\Delta$ between said pickup coils are set to satisfy the condition $10 \leq h/\Delta \leq 20$.

10. An apparatus for inspecting damage of a material comprising at least one pair of pickup coils for detecting magnetic flux signals from an object to be inspected, at least one SQUID for receiving signals from said pickup coils and a processing unit for receiving and processing an output signal from the SQUID, said pickup coils being disposed at different distances from said object, said SQUID being connected to said coil pair, and said processing unit decides the form of a defect of said object from a measured output value of said SQUID on the basis of a predetermined relationship between SQUID output, distances between pickup coils and an object, and a form of defect of an object.

11. An apparatus according to claim 10, wherein said processing unit determines the area of said defect from the decided form of said defect on the basis of a predetermined relationship between area of defect and SQUID output.

12. An apparatus according to claim 10, wherein a distance between said object and said pickup coils is set to be between 20 and 100 mm and an interval between said pickup coils is set to be between 2 and 10 mm.

13. An apparatus according to claim 10, wherein a distance h between said object and said pickup coils and an interval $\Delta$ between said pickup coils are set to satisfy the condition of $10 \leq h/\Delta \leq 20$.

14. An apparatus for inspecting damage of a material comprising a plurality of pickup coils for detecting magnetic flux signals from an object to be inspected, a plurality of SQUIDs, each of the SQUIDs being connected for receiving a signal from a respective pickup coil, an a processing unit for receiving ad processing output signals from the SQUIDs, said pickup coils being disposed at different distances from said object, and said processing unit performs an operation to minimize a background signal caused by the surface geometry of said object by producing a difference between outputs of said SQUIDs.

15. An apparatus according to claim 14, wherein a distance between said object and said pickup coils is set to be between 20 and 100 mm and an interval between said pickup coils is set to be between 2 to 10 mm.

16. An apparatus according to claim 14, wherein a distance h between said object and said pickup coils and an interval $\Delta$ between said pickup coils are set to satisfy the condition of $10 \leq h/\Delta \leq 20$.

17. An apparatus for inspecting degradation/damage of a material comprising:

a DC magnet for applying a DC magnetic field to an object to be inspected so as to enable measurement of a magnetic hysteresis loop of said object;

an AC magnet for applying a small AC magnetic field to said object to enable measurement of a minor magnetic hysteresis loop of said object;

a magnetic sensor measuring said magnetic hysteresis loop and said minor magnetic hysteresis loop of said object; and a processing unit for detecting degradation/damage from measurement data of a magnetic characteristic of said object from said magnetic sensor and deciding the degree of degradation/damage;

wherein said AC magnet and said magnetic sensor are arranged above a surface of said object and said DC magnet is arranged at a position higher than said AC magnet and said magnetic sensor.

* * * * *